United States Patent
McKay

(10) Patent No.: US 8,202,531 B2
(45) Date of Patent: Jun. 19, 2012

(54) DRUG DEPOTS HAVING ONE OR MORE ANCHORING MEMBERS

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 490 days.

(21) Appl. No.: 12/178,106

(22) Filed: Jul. 23, 2008

(65) Prior Publication Data

US 2010/0021516 A1     Jan. 28, 2010

(51) Int. Cl.
*A61F 2/00*          (2006.01)

(52) U.S. Cl. ........................ 424/426; 623/11.11

(58) Field of Classification Search .................. None
See application file for complete search history.

(56) References Cited

U.S. PATENT DOCUMENTS

| | | | |
|---|---|---|---|
| 4,624,255 A | 11/1986 | Schenck et al. | |
| 4,863,457 A | 9/1989 | Lee | |
| 5,756,127 A * | 5/1998 | Grisoni et al. | 424/489 |
| 5,868,789 A | 2/1999 | Huebner | |
| 6,530,934 B1 * | 3/2003 | Jacobsen et al. | 606/157 |
| 6,756,058 B2 | 6/2004 | Brubaker et al. | |
| 6,974,462 B2 | 12/2005 | Sater | |
| 6,989,034 B2 * | 1/2006 | Hammer et al. | 623/23.72 |
| 7,144,412 B2 | 12/2006 | Wolf et al. | |
| 7,166,570 B2 | 1/2007 | Hunter | |
| 7,235,043 B2 | 6/2007 | Gellman | |
| 7,361,168 B2 | 4/2008 | Makower et al. | |
| 2002/0016562 A1 | 2/2002 | Cormier et al. | |
| 2003/0039689 A1 * | 2/2003 | Chen et al. | 424/468 |
| 2003/0204191 A1 | 10/2003 | Sater | |
| 2004/0193137 A1 | 9/2004 | Bates | |
| 2005/0101915 A1 | 5/2005 | Morris et al. | |
| 2006/0020247 A1 * | 1/2006 | Kagan et al. | 604/264 |
| 2006/0057198 A1 * | 3/2006 | Lewis et al. | 424/469 |
| 2006/0106361 A1 | 5/2006 | Muni | |
| 2007/0243225 A1 | 10/2007 | McKay | |
| 2007/0243228 A1 | 10/2007 | McKay | |

FOREIGN PATENT DOCUMENTS

WO    2007121288    10/2007

OTHER PUBLICATIONS

Lai et al; "Sutures and needles" from emedicine.medscape.com (http://emedicine.medscape.com/article/884838-overview) (p. 6).*
International Search Report and Written Opinion for Application PCT/US2009/050477 mailed on Mar. 8, 2010, 12 pages.

* cited by examiner

*Primary Examiner* — Bethany Barham

(57) ABSTRACT

A drug depot implantable at or near a target tissue site beneath the skin of a patient is provided, the drug depot comprising a therapeutically effective amount of a drug and at least one surface adapted to receive one or more anchoring members so as to limit movement of the drug depot at or near the target tissue site, wherein at least one region of the drug depot is capable of releasing the therapeutically effective amount of the drug over a period of at least one day. In some embodiments, the drug depot provided can include an effective amount of at least analgesic and at least one anti-inflammatory agent at or near a target site, and can reduce, prevent or treat inflammation and/or pain, particularly postoperative pain.

6 Claims, 18 Drawing Sheets

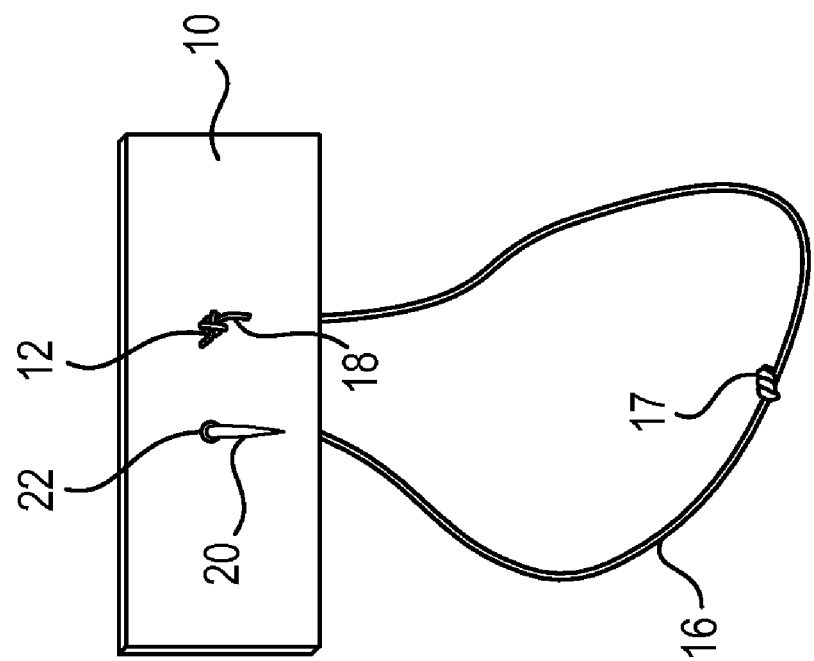

DRUG DEPOTS HAVING ONE OR MORE ANCHORING MEMBERS

BACKGROUND

Drugs may be delivered to patients by a variety of methods including oral, intravenous, intramuscular, inhalation, topical, subcutaneous delivery or delivery directly or locally to the treatment site (e.g., intrathecally, intraspinally, intraarticularly, etc.). The method of delivery chosen depends, among other things, upon the condition being treated, desired therapeutic concentration of the drug to be achieved in the patient and the duration of drug concentration that must be maintained.

Recently, drug depots have been developed which allow a drug to be introduced or administered to sites beneath the skin of a patient so that the drug is slowly released over a long period of time. Such drug depots allow the drug to be released from the depot in a relatively uniform dose over weeks, months or even years. This method of administering drugs is becoming especially important for contraceptives and cancer drugs that are implanted subcutaneously.

Sometimes, after the drug depot is implanted at the treatment site, the drug depot may migrate from the implant site prior to surgical closure (e.g., floats off in blood or shifts as tissues are repositioned during surgical site closure) or as physiological conditions change (e.g., repair and regeneration of cells, tissue ingrowth, movement at implant site, etc.). At times, this may reduce efficacy of the drug as the drug depot migrates away from the implant site and lodges in a distant site. If this occurs, the drug depot will have to be removed from the distant site and have to be reinserted causing additional physical and psychological trauma to a patient. In some cases, if the drug depot migrates into a joint, the drug depot may inhibit movement. In more severe cases, if the drug depot migrates, it may restrict blood flow causing an ischemic event (e.g., embolism, necrosis, infarction, etc.), which could be detrimental to the patient.

Postoperative pain tends to be a difficult condition to treat and may be detrimental to the patient if not properly treated. The site of the surgery has a profound effect upon the degree of postoperative pain a patient may suffer. In general, operations on the thorax and upper abdomen are more painful than operations on the lower abdomen, which in turn are more painful than peripheral operations on the limbs. However, any operation involving a body cavity, large joint surfaces, the spine or deep tissues should be regarded as painful. In particular, operations on the thorax or upper abdomen may produce widespread changes in pulmonary function, an increase in abdominal muscle tone and an associated decrease in diaphragmatic function. The result will be an inability to cough and clear secretions, which may lead to lung collapse and pneumonia. Prolonged pain can reduce physical activity and lead to venous stasis and an increased risk of deep vein thrombosis and consequently pulmonary embolism. In addition, there can be widespread effects on gut and urinary tract motility, which may lead in turn to postoperative ileus, nausea, vomiting and urinary retention. These problems are unpleasant for the patient and may prolong hospital stay and are exacerbated if after implantation the drug depot migrates away from the implant site.

New drug depot compositions and methods are needed, which can easily allow accurate and precise placement of a drug depot. When implanting several drug depots at a time, drug depot compositions and methods are needed that accurately and precisely allow placement of the drug depot in a manner that optimizes location, accurate spacing, and drug distribution. New drug depot compositions and methods are also needed to effectively treat post-operative pain.

SUMMARY

A new implantable drug depot that improves drug efficacy and reduces unwanted migration of the drug depot is provided. In various embodiments, new drug depot compositions and methods are provided that effectively prevent, treat or reduce postoperative pain and/or inflammation by providing consistent analgesic and/or anti-inflammatory efficacy at the target tissue site of pain generation. In various embodiments, the drug depot is pre-attached to a needle and suture and includes a tie-off system, which easily allows the surgeon to suture the depot to the target tissue site of pain generation.

In various embodiments, a drug depot is provided that is pre-knotted and pre-threaded so that all the surgeon has to do is pass the needle through the soft tissue and pull the needle and suture back through the drug depot. The knot will lock the depot in place and all the surgeon needs to do is cut the suture. This "pull and cut" system eliminates some surgical steps (e.g., knotting) and reduces the length of time during surgery.

In some embodiments, a drug depot implantable at or near a target tissue site beneath the skin of a patient is provided, the drug depot comprising a therapeutically effective amount of a drug and at least one surface adapted to receive one or more anchoring members so as to limit movement of the drug depot at or near the target tissue site, wherein at least one region of the drug depot is capable of releasing the therapeutically effective amount of the drug over a period of at least one day.

In some embodiments, the at least one surface of the drug depot comprises one or more channels, holes, grooves, slits, loops, hooks, barbs, posts and/or clips adapted to receive the one or more anchoring members. In some embodiments, the drug depot comprises one or more sutures, yarns, threads, lines, and/or staples used as the anchoring members.

In some embodiments, a drug depot implantable at or near a target tissue site beneath the skin of a patient is provided, the drug depot comprising a therapeutically effective amount of a drug and one or more channels adapted to receive one or more sutures so as to limit movement of the drug depot at or near the target tissue site, wherein the drug depot is capable of releasing the therapeutically effective amount of the drug over a period of at least one day.

In some embodiments, a drug depot implantable at or near a target tissue site beneath the skin of a patient is provided, the drug depot comprising a therapeutically effective amount of a drug and one or more channels adapted to receive one or more sutures, the one or more sutures comprising at least two regions, each region having a surface larger than the one or more channels so that when the suture is passed through the one or more channels movement of the drug depot is limited at or near the target tissue site, wherein the drug depot is capable of releasing the therapeutically effective amount of the drug over a period of at least one day.

In some embodiments, a drug depot implantable at or near a target tissue site beneath the skin of a patient is provided, the drug depot comprising a therapeutically effective amount of a drug and one or more channels adapted to receive one or more sutures, the one or more sutures comprising at least two knotted, rimmed, beaded, ridged, or clipped areas spaced apart from each other, each knotted, rimmed, beaded, ridged, or clipped area having a surface larger than the one or more channels so that when the suture is passed through the one or more channels the depot is locked in place and movement of the drug depot is limited at or near the target tissue site, wherein the drug depot is capable of releasing the therapeutically effective amount of the drug over a period of at least one day.

In some embodiments, a method of treating or preventing postoperative pain or inflammation in a patient in need of such treatment is provided, the method comprising suturing one or more biodegradable drug depots comprising a therapeutically effective amount of an analgesic and/or anti-inflammatory agent or pharmaceutically acceptable salt thereof at or near a target tissue site beneath the skin, wherein the drug depot comprises at least one surface adapted to receive one or more sutures so as to limit movement of the drug depot at or near the target tissue site and the drug depot is capable of releasing the analgesic and/or anti-inflammatory agent or pharmaceutically acceptable salt thereof over a period of at least one day.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

FIG. 5A illustrates a front view of one embodiment of the implantable drug depot having two surfaces, in this case two channels, disposed at different ends of the drug depot that can receive a suture. The needle is passed through tissue then through the second channel of the depot. The surgeon pulls the suture through the channel to lock the depot in place at or near a target tissue site.

Figure 1:
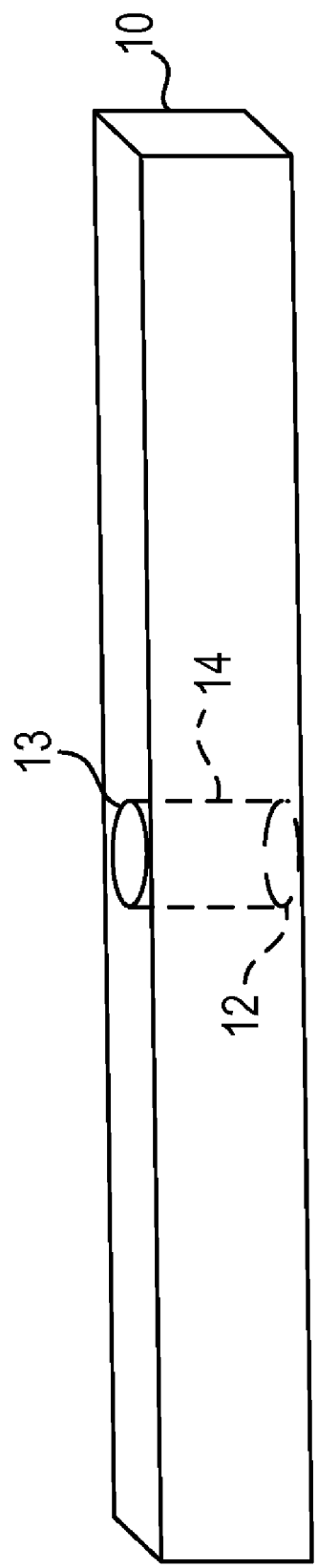
FIG. 1 is a side sectional view of one embodiment of the implantable drug depot having a surface in this case a channel disposed in the center of the depot to receive one or more anchoring members, such as for example, a suture or staple.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

Definitions

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

"Analgesic" refers to an agent or compound that can reduce, relieve or eliminate pain. Examples of analgesic agents include but are not limited to acetaminophen, a local anesthetic, such as for example, lidocaine, bupivicaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, mepiridine, methadone, morphine, nalbuphine, opium, oxycodone, papaveretum, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof.

The phrase "anti-inflammatory agent" refers to an agent or compound that has anti-inflammatory effects. These agents may remedy pain by reducing inflammation. Examples of anti-inflammatory agents include, but are not limited to, a statin, sulindac, sulfasalazine, naroxyn, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketorolac, clonidine, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof. Anti-inflammatory agents also include other compounds such as steroids, such as for example, fluocinolone, cortisol, cortisone, hydrocortisone, fludrocortisone, prednisone, prednisolone, methylprednisolone, triamcinolone, betamethasone, dexamethasone, beclomethasone, fluticasone interleukin-1 receptor antagonists, thalidomide (a TNF-α release inhibitor), thalidomide analogues (which reduce TNF-α production by macrophages), bone morphogenetic protein (BMP) type 2 or BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), guanidinoethyldisulfide, or a combination thereof.

Exemplary anti-inflammatory agents include, for example, naproxen; diclofenac; celecoxib; sulindac; diflunisal; piroxicam; indomethacin; etodolac; meloxicam; ibuprofen; ketoprofen; r-flurbiprofen; mefenamic; nabumetone; tolmetin, and sodium salts of each of the foregoing; ketorolac bromethamine; ketorolac tromethamine; ketorolac acid; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, 1, and racemic isomers); methyl, ethyl, propyl, isopropyl, n-butyl, sec-butyl, t-butyl, esters of acetylsalicylic acid; tenoxicam; aceclofenac; nimesulide; nepafenac; amfenac; bromfenac; flufenamate; phenylbutazone, or a combination thereof.

Exemplary steroids include, for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

Examples of a useful statin for treatment of pain and/or inflammation include, but is not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin. Anti-inflammatory agents also include those with anti-inflammatory properties, such as, for example, amitriptyline, carbamazepine, gabapentin, pregabalin, clonidine, or a combination thereof.

Unless otherwise specified or apparent from context, where this specification and the set of claims that follows refer to a drug (e.g., an anti-inflammatory agent, analgesic, and the like) the inventor(s) are also referring to a pharmaceutically acceptable salt of the drug including stereoisomers. Pharmaceutically acceptable salts include those salt-forming acids and bases that do not substantially increase the toxicity of the compound. Some examples of potentially suitable salts include salts of alkali metals such as magnesium, calcium, sodium, potassium and ammonium, salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

"Treating" or treatment of a disease or condition refers to executing a protocol, which may include administering one or more drugs to a patient (human, normal or otherwise, or other mammal), in an effort to alleviate signs or symptoms of the disease. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms, does not require a cure, and specifically includes protocols that have only a marginal effect on the patient. "Reducing pain" includes a decrease in pain and does not require complete alleviation of pain signs or symptoms, and does not require a cure. In various embodiments, reducing pain includes even a marginal decrease in pain. By way of example, the administration of the effective dosages of at least one analgesic agent and at least one anti-inflammatory agent may be used to prevent, treat or relieve the symptoms of pain and/or inflammation.

"Localized" delivery includes delivery where one or more drugs are deposited within a tissue, for example, a nerve root of the nervous system or a region of the brain, or in close proximity (within about 10 cm, or preferably within about 5 cm, for example) thereto. A "targeted delivery system" provides delivery of one or more drugs depots having a quantity of therapeutic agent that can be deposited at or near the target site as needed for treatment of pain, inflammation or other disease or condition.

The term "mammal" refers to organisms from the taxonomy class "mammalian," including but not limited to humans, other primates such as chimpanzees, apes, orangutans and monkeys, rats, mice, cats, dogs, cows, horses, etc. In various embodiments, the mammal is a human patient.

Drug Depot

In some embodiments, a drug depot implantable at or near a target tissue site beneath the skin of a patient is provided, the drug depot comprising a therapeutically effective amount of a drug and at least one surface adapted to receive one or more anchoring members so as to limit movement of the drug depot at or near the target tissue site, wherein at least one region of the drug depot is capable of releasing the therapeutically effective amount of the drug over a period of at least one day.

A "drug depot" comprises the composition in which at least one active pharmaceutical ingredient or drug is administered to the body. Thus, a drug depot may comprise a physical structure to facilitate implantation and retention in a desired site (e.g., a disc space, a spinal canal, a tissue of the patient, particularly at or near a site of surgery, pain, or site of inflammation, etc.). The drug depot also comprises the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 0.1 cm to about 5 cm from the implant site, and comprises at least one anti-inflammatory agent or its pharmaceutically acceptable salt and/or at least one analgesic agent or its pharmaceutically acceptable salt.

A "depot" includes but is not limited to capsules, coatings, matrices, wafers, sheets, strips, ribbons, pills, pellets, or other pharmaceutical delivery or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof. Typically, the depot will be a solid or semi-solid formulation comprised of a biocompatible material that can be biodegradable. The term "solid" is intended to mean a rigid material, while "semi-solid" is intended to mean a material that has some degree of flexibility, thereby allowing the depot to bend and conform to the surrounding tissue requirements.

A "therapeutically effective amount" or "effective amount" is such that when administered, the drug results in alteration of the biological activity, such as, for example, inhibition of inflammation, reduction or alleviation of pain, improvement in the condition through muscle relaxation, etc. The dosage administered to a patient can unless otherwise specified or apparent from context be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustain release surfaces.

The phrases "sustained release" or "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s). As persons of ordinary skill are aware, sustained release formulations may be, by way of example, be created as films, slabs, pellets, microparticles, microspheres, microcapsules, spheroids, shaped derivatives and paste. Further, the formulations may be used in conjunction with any implantable, or insertable system that a person of ordinary skill would appreciate as useful in connection with embodiments herein including but not limited to parenteral formulations, microcapsules, pastes, implantable rods, pellets, plates or fibers, etc.

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug. Immediate release refers to the release of drug within a short time period following administration, e.g., generally within a few minutes to about 1 to 2 hours.

The phrase "release rate profile" refers to the percentage of active ingredient that is released over fixed units of time, e.g., mcg/hr, mcg/day, mg/hr, mg/day, 10% per day for ten days, and the like. As persons of ordinary skill know, a release rate profile may be but need not be linear. By way of a non-limiting example, the drug depot may be a pellet that releases at least one analgesic agent in a bolus dose and at least one anti-inflammatory agent over a period of time.

The term "biodegradable" includes that all or parts of the drug depot will degrade over time by the action of enzymes, by hydrolytic action and/or by other similar mechanisms in the human body. In various embodiments, "biodegradable" includes that the depot can break down or degrade within the body to non-toxic components after or while a therapeutic agent has been or is being released. By "bioerodible" it is meant that the depot will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

The depot and/or anchoring members may comprise non-biodegradable material. Examples of non-biodegradable polymers include, but are not limited to, various cellulose derivatives (carboxymethyl cellulose, cellulose acetate, cellulose acetate propionate, ethyl cellulose, hydroxypropyl methyl cellulose, hydroxyalkyl methyl celluloses, and alkyl celluloses), silicon and silicon-based polymers (such as polydimethylsiloxane), polyethylene-co-(vinyl acetate), poloxamer, polyvinylpyrrolidone, poloxamine, polypropylene, polyamide, polyacetal, polyester, poly ethylene-chlorotrifluoroethylene, polytetrafluoroethylene (PTFE or "Teflon™"), styrene butadiene rubber, polyethylene, polypropylene, polyphenylene oxide-polystyrene, poly-α-chloro-p-xylene, polymethylpentene, polysulfone, non-degradable ethylene-vinyl acetate (e.g., ethylene vinyl acetate disks and poly(ethylene-co-vinyl acetate)), and other related biostable polymers.

Non-resorbable polymers can also include, but are not limited to, delrin, polyurethane, copolymers of silicone and polyurethane, polyolefins (such as polyisobutylene and polyisoprene), acrylamides (such as polyacrylic acid and poly (acrylonitrile-acrylic acid)), neoprene, nitrile, acrylates (such as polyacrylates, poly(2-hydroxy ethyl methacrylate), methyl methacrylate, 2-hydroxyethyl methacrylate, and copolymers of acrylates with N-vinyl pyrrolidone), N-vinyl lactams, polyacrylonitrile, glucomannan gel, vulcanized rubber and combinations thereof. Examples of polyurethanes include thermoplastic polyurethanes, aliphatic polyurethanes, segmented polyurethanes, hydrophilic polyurethanes, polyether-urethane, polycarbonate-urethane and silicone polyether-urethane. Other suitable non-resorbable material include, but are not limited to, lightly or highly cross-linked biocompatible homopolymers and copolymers of hydrophilic monomers such as 2-hydroxyalkyl acrylates and methacrylates, N-vinyl monomers, and ethylenically unsaturated acids and bases; polycyanoacrylate, polyethylene oxide-polypropylene glycol block copolymers, polygalacturonic acid, polyvinyl pyrrolidone, polyvinyl acetate, polyalkylene glycols, polyethylene oxide, collagen, sulfonated polymers, vinyl ether monomers or polymers, alginate, polyvinyl amines, polyvinyl pyridine, and polyvinyl imidazole. Depending on the amount of crosslinking within the bioresorbable polymers, the degradation time of the polymer can be reduced, thus making the polymer, for the purpose of this invention, appear to be non-resorbable over the time frame of the use of the material for this invention.

The phrase "pain management medication" includes one or more therapeutic agents that are administered to prevent, alleviate or remove pain entirely. These include anti-inflammatory agents, muscle relaxants, analgesics, anesthetics, narcotics, and so forth, and combinations thereof.

In various embodiments, the depot can be designed to cause an initial burst dose of one or more therapeutic agents within the first 24 hours after implantation. "Initial burst" or "burst effect" or "bolus dose" or "pulse dose" refer to the release of therapeutic agent from the depot during the first 24 hours after the depot comes in contact with an aqueous fluid (e.g., synovial fluid, cerebral spinal fluid, etc.). The burst effect may be an immediate release. The "burst effect" is believed to be due to the increased release of therapeutic agent from the depot. The initial burst effect or bolus dose may be determined beforehand by formulating the depot by calculating the quotient obtained by dividing (i) the effective amount by weight of therapeutic agent to be released from the depot or region in a predetermined initial period of time after implantation of the depot, by (ii) the total amount of therapeutic agent that is to be delivered from an implanted composition. It is understood that the initial burst may vary depending on the shape and surface area of the implant.

The burst effect with respect to the region or depot, in various embodiments, can be designed so that a larger initial dose may be released over a short period of time to achieve the desired effect. For example, if a drug depot is designed to release 15 mg of morphine per 48 hours, then the initial burst dose or bolus dose region or depot will be designed to release a percentage of the dose within the first 24 hours (e.g., 10 mg of morphine or 66% of the 48 hour dose within 24 hours). Thus, the burst effect of the drug depot or region releases more therapeutic agent than the sustained release region or depot.

A region or depot that utilizes a burst effect or bolus dose will release more therapeutic agent (e.g., analgesic and/or anti-inflammatory) than the sustained release region or depot. For example, particularly with painful chronic conditions including rheumatoid arthritis, osteoarthritis, a spinal disc herniation (e.g., sciatica), carpal/tarsal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, spondilothesis, stenosis, discogenic back pain, and joint pain or the like, the initial burst effect of the drug depot or region of the drug depot will be advantageous as it will provide more immediate pain and/or inflammation relief as a bolus dose of drug will be released at or near the target tissue site and provide the desired reducing, or alleviation of signs or symptoms of pain and/or inflammation. For example, the drug depot or region of the drug depot may release 51%, 52%, 53%, 54%, 55%, % 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of the daily dose within the first one to twelve hours to reduce, prevent or treat pain and/or inflammation. The pain and/or inflammation may also be postoperative pain following surgery.

The drug depot can comprise at least one analgesic agent or its pharmaceutically acceptable salt and/or at least one anti-inflammatory agent or its pharmaceutically acceptable salt may be co-administered with a muscle relaxant. Co-administration may involve administering at the same time in separate drug depots or formulating together in the same drug depot.

Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The drug depot may also comprise other therapeutic agents or active ingredients in addition to the at least one analgesic agent or its pharmaceutically acceptable salt and at least one anti-inflammatory agent or its pharmaceutically acceptable salt. Suitable additional therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents that may be co-administered with the anti-inflammatory agent and analgesic agent include IL-1 inhibitors, such Kineret® (anakinra) which is a recombinant, non-glycosylated form of the human inerleukin-1 receptor antagonist (IL-lRa), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. It is contemplated that where desirable a pegylated form of the above may be used. Examples of other therapeutic agents include NF kappa B inhibitors such as glucocorticoids, antioxidants, such as dilhiocarbamate.

Specific examples of additional therapeutic agents suitable for use include, but are not limited to, an anabolic growth factor or anti-catabolic growth factor, analgesic agent, or an osteoinductive growth factor or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

Suitable analgesic agents include, but are not limited to, acetaminophen, bupivicaine, opioid analgesics such as amitriptyline, carbamazepine, gabapentin, pregabalin, clonidine, opioid analgesics or a combination thereof. Opioid analgesics include, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol or a combination thereof.

For each of the anti-inflammatory agents and analgesic agents, in some embodiments, the release of each compound may be for at least one, at least two, at least three, at least four, at least five, at least six, at least seven, at least eight, at least nine, at least ten, at least eleven, at least twelve, at least thirteen, at least fourteen, or at least fifteen days, or longer.

The drug depot may also be administered with non-active ingredients. These non-active ingredients may have multi-functional purposes including the carrying, stabilizing and controlling the release of the therapeutic agent(s). The sustained release process, for example, may be by a solution-diffusion mechanism or it may be governed by an erosion-sustained process.

In various embodiments, the non-active ingredients will be durable within the tissue site for a period of time equal to (for biodegradable components) or greater than (for non-biodegradable components) the planned period of drug delivery. For example, the depot material may have a melting point or glass transition temperature close to or higher than body temperature, but lower than the decomposition or degradation temperature of the therapeutic agent. However, the pre-determined erosion of the depot material can also be used to provide for slow release of the loaded therapeutic agent(s).

In various embodiments, the drug depot may not be biodegradable or comprise material that is not biodegradable. Non-biodegradable polymers include, but are not limited to, various cellulose derivatives (carboxymethyl cellulose, cellulose acetate, cellulose acetate propionate, ethyl cellulose, hydroxypropyl methyl cellulose, hydroxyalkyl methyl celluloses, and alkyl celluloses), silicon and silicon-based polymers (such as polydimethylsiloxane), polyethylene-co-(vinyl acetate), poloxamer, polyvinylpyrrolidone, poloxamine, polypropylene, polyamide, polyacetal, polyester, poly ethylene-chlorotrifluoroethylene, polytetrafluoroethylene (PTFE or "Teflon™"), styrene butadiene rubber, polyethylene, polypropylene, polyphenylene oxide-polystyrene, poly-α-chloro-p-xylene, polymethylpentene, polysulfone, non-degradable ethylene-vinyl acetate (e.g., ethylene vinyl acetate disks and poly(ethylene-co-vinyl acetate)), and other related biostable polymers or combinations thereof.

The drug depot may comprise non-resorbable polymers as well. These non-resorbable polymers can include, but are not limited to, delrin, polyurethane, copolymers of silicone and polyurethane, polyolefins (such as polyisobutylene and polyisoprene), acrylamides (such as polyacrylic acid and poly (acrylonitrile-acrylic acid)), neoprene, nitrile, acrylates (such as polyacrylates, poly(2-hydroxy ethyl methacrylate), methyl methacrylate, 2-hydroxyethyl methacrylate, and copolymers of acrylates with N-vinyl pyrrolidone), N-vinyl lactams, polyacrylonitrile, glucomannan gel, vulcanized rubber and combinations thereof. Examples of polyurethanes include thermoplastic polyurethanes, aliphatic polyurethanes, segmented polyurethanes, hydrophilic polyurethanes, polyether-urethane, polycarbonate-urethane and silicone polyether-urethane. Typically, the non-degradable drug depots may need to be removed.

In some instance, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

In various embodiments, the depot may comprise a bioabsorbable, and/or a biodegradable biopolymer that may provide immediate release, or sustained release of the at least one analgesic agent and at least one anti-inflammatory agent. Examples of suitable sustained release biopolymers include but are not limited to poly (alpha-hydroxy acids), poly (lactide-co-glycolide) (PLGA or PLG), polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, poly(glycolide-,-caprolactone), ,-caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the resulting formulations.

Where different combinations of polymers are used (bi, tri (e.g., PLGA-PEO-PLGA) or terpolymers), they may be used in different molar ratios, 1:1, 2:1, 3:1, 4:1, 5:1, 6:1, 7:1, 8:1, 9:1, or 10:1. For example, for a 130-day release drug depot, the polymer make up is 50:50 PLGA to 100 PLA. The molecular weight range is 0.45 to 0.8 dI/g.

In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

In some embodiments, the at least one biodegradable polymer comprises poly(lactic-co-glycolic acid) (PLA) or poly (orthoester) (POE) or a combination thereof. The poly(lactic-co-glycolic acid) may comprise a mixture of polyglycolide (PGA) and polylactide and in some embodiments, in the mixture, there is more polylactide than polyglycolide. In various other embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer being polyglycolide.

In some embodiments, the biodegradable polymer comprises at least 10 wt %, at least 50 wt. %, at least 60 wt. %, at least 70 wt. %, at least 80 wt. %, at least 85 wt. %, at least 90 wt. %, at least 95 wt. %, or at least 99 wt. % of the formulation. In some embodiments, the at least one biodegradable polymer and the analgesic and the anti-inflammatory are the only components of the pharmaceutical formulation.

In some embodiments, at least 75% of the particles have a size from about 1 micrometer to about 250 micrometers. In some embodiments, at least 85% of the particles have a size from about 1 micrometer to about 100 micrometers. In some embodiments, at least 95% of the particles have a size from about 1 micrometer to about 30 micrometers. In some embodiments, all of the particles have a size from about 1 micrometer to about 30 micrometers.

In some embodiments, at least 75% of the particles have a size from about 5 micrometer to about 20 micrometers. In some embodiments, at least 85% of the particles have a size from about 5 micrometers to about 20 micrometers. In some embodiments, at least 95% of the particles have a size from about 5 micrometer to about 20 micrometers. In some embodiments, all of the particles have a size from about 5 micrometer to about 20 micrometers.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methylparaben, polyvinyl alcohol and phenylethyl alcohol; solubility adjusting agents; stabilizers; and/or cohesion modifiers. Typically, any such inactive materials will be present within the range of 0-75 wt %, and more typically within the range of 0-30 wt %. If the depot is to be placed in the spinal area, in various embodiments, the depot may comprise sterile preservative free material. The depot can be different sizes, shapes and configurations, such as for example, strip, rod, sheet, mesh, or the like. There are several factors that can be taken into consideration in determining the size, shape and configuration of the drug depot. For example, both the size and shape may allow for ease in positioning the drug depot at the target tissue site that is selected as the implantation site. In addition, the shape and size of the system should be selected so as to minimize or prevent the drug depot from moving after implantation or injection. In various embodiments, the drug depot can be shaped like a pellet, a sphere, a cylinder such as a rod, a flat surface such as a disc, film or sheet, strip, rod, mesh, or the like. Flexibility may be a consideration so as to facilitate placement of the drug depot. In various embodiments, the drug depot can be different sizes, for example, the drug depot may be a length of from about 2 to 4 cm and width of from about 1-2 cm and thickness of from about 0.25 to 1 mm, or length of from about 0.5 mm to 5 cm and have a diameter of from about 0.01 to about 2 mm. In various embodiments, the depot is a strip having dimensions of 2.5 cm×1.5 cm×0.5 mm. In various embodiments, the drug depot may have a layer thickness of from about 0.005 to 1.0 mm, such as, for example, from 0.05 to 0.75 mm.

In some embodiments, the surgeon accesses the target tissue site and threads a suture using a needle into the drug depot through the one or more channels, slits, loops, and/or clips or ties the suture around the one or more grooves, hooks, barbs, posts and/or clips of the drug depot then passes the suture and needle through the target tissue site and then anchors the drug depot at or near the target tissue site by tying a knot so as to limit the movement of the drug depot, even in areas where there is excessive blood flow, shifting of tissues during surgical site closure, or great movement of the tissue (e.g., in a joint or muscle area). The needle is then removed and the suture cut and knotted leaving the suture and the drug depot in the desired position.

FIG. 1 is a side sectional view of one embodiment of the implantable drug depot 10 having surface openings 12 and 13 that lead to channel 14 disposed in the center of the depot and adapted to receive one or more anchoring members, such as for example, a suture, yarn, thread, line or staple, which can pass into the target tissue site and anchor the drug depot at or near the target tissue site. Thus, in various embodiments, the surface can be a sufficient size to receive the anchoring member (e.g., suture, yarn, thread, line or staple). Although the drug depot is shown as a rectangular shape. It will be understood by one or ordinary skill in the art that the drug depot can be any shape (e.g., pellet, oval, strip, rod, sheet, mesh, or the like). It will also be understood by one of ordinary skill in the art that the attachment surface of the drug depot can include one or more ports, grooves, slits, loops, hooks, barbs, posts and/or clips instead of the channel (shown in FIG. 1) adapted to receive the one or more anchoring members.

The attachment surface of the drug depot may be an extension from the drug depot 10. It will be understood by those of ordinary skill in the art that the one or more channels, grooves, slits, loops, hooks, barbs, posts and/or clips can be made of the same or different material than the drug depot. It will also be understood by those of ordinary skill in the art that the one or more anchoring members (e.g., suture, yarn, line, etc.) can be made of the same or different material as the drug depot.

Surgical procedures can be used to attach the drug depot at or near the target tissue site. In such applications, a suture is threaded through the channel disposed through the drug depot. The suture anchors the drug depot 10 to the target tissue site.

The drug depot may be attached to the suture before or after the drug depot is affixed to the anatomical structure or target tissue plane. By pre-attaching the needle and/or suture to the drug depot, surgical steps are eliminated as the suture does not need to be threaded through the drug depot and the surgery can be performed at a quicker pace.

In various embodiments, the drug depot can be positioned inside the body of a patient under the skin and against a tissue plane, and a needle having the suture is passed through the drug depot surface and then into the anatomical site to anchor the drug depot at or near the target tissue site. After the needle is pierced through a body tissue, the needle is cut off, and knots are fastened according to surgical fastening methods.

Figure 1A:
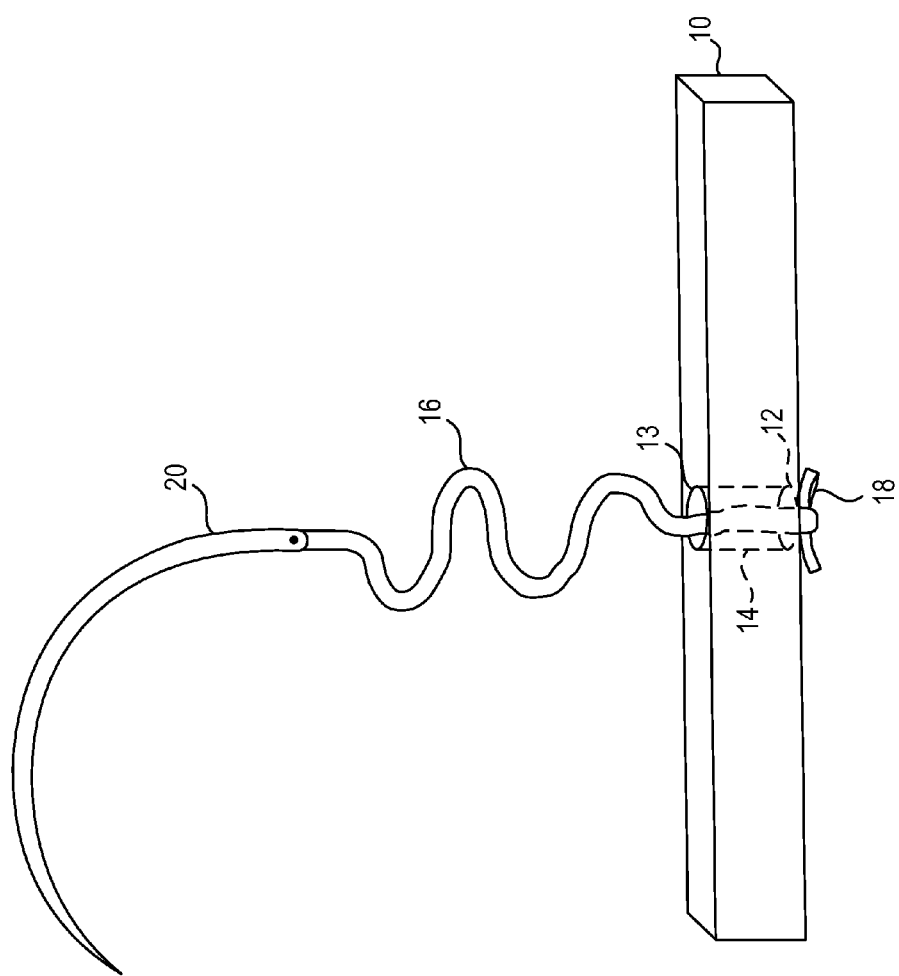
FIG. 1A is a side sectional view of one embodiment of the implantable drug depot having a surface, in this case a channel, disposed in the center of the depot to receive a suture as the anchoring member that allows the drug depot to be sutured at or near a target tissue site.

FIG. 1A is a side sectional view of one embodiment of the implantable drug depot 10 having surface openings 12 and 13 that lead to channel 14, which is adapted to receive a needle 20 having an anchoring member such as a suture 16 attached thereto that is passed through opening 12 through channel 14 and out of opening 13 of the drug depot. The needle and suture extend from the channel, where the needle can pierce a target tissue site. Here the suture 16 can comprise a portion or region (e.g., knot, rim, bead, clip, ridge, tab, or the like) that allows the suture to be pulled taut while holding the suture in place. This portion of the suture prevents both ends of the suture from passing through the drug depot. Shown in FIG. 1A is a knot 18, that the surgeon may tie or the knot may be made beforehand when the drug depot is pre-threaded with suture, yarn, thread, line, wire, or the like. In this way, the surgeon only needs to pierce the target tissue site with the needle and tie the drug depot to the target tissue site via a knot, without fear that if the suture is pulled too hard, the suture will be pulled out of the depot.

Although a knot is shown in FIG. 1A, it will be understood that the suture can have a portion that will be larger than the opening of the channel so that one end of the suture can not pass through the drug depot. In this way the suture can be pulled taut. Thus, one end of the suture can comprise a knot, rim, bead or clip that is larger than the channel to prevent the suture from being pulled through the channel of the drug depot.

Figure 2:
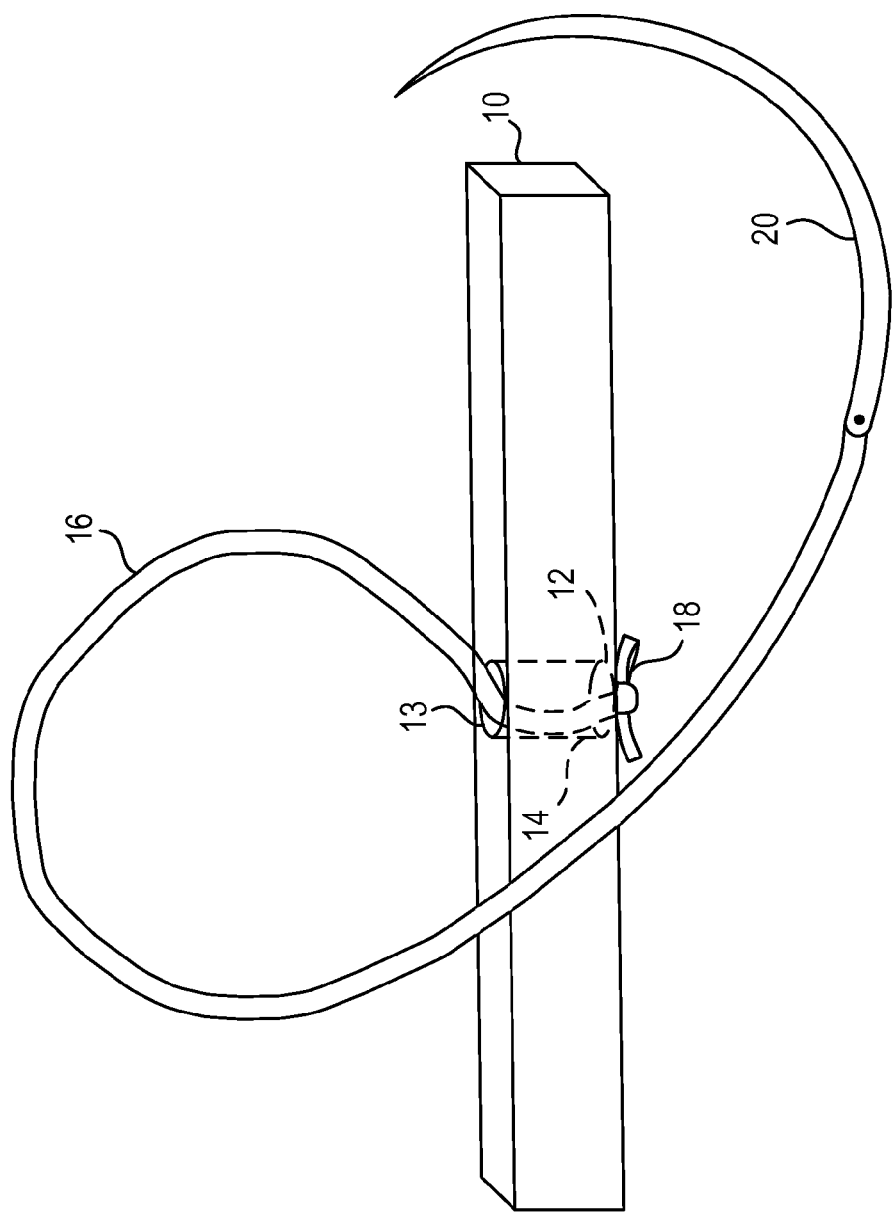
FIG. 2 is a side sectional view of one embodiment of the implantable drug depot having a surface, in this case a channel, disposed in the center of the depot to receive a suture as the anchoring member that allows the drug depot to be sutured at or near a target tissue site.

FIG. 2 is a side sectional view of one embodiment of the implantable drug depot 10 having surface openings 12 and 13 that lead to channel 14, which is adapted to receive a needle 20 having an anchoring member such as a suture 16 attached thereto that is passed through opening 12 through channel 14 and out of opening 13 of the drug depot. This is one example of a pre-threaded drug depot design. The needle and suture extend from the channel, where the needle can pierce a target tissue site. Here the suture 16 can be looped and knotted at, near or against a target tissue. Shown in FIG. 2 is a knot 18, that the surgeon may tie or the knot may be made beforehand when the drug depot is pre-threaded with suture, yarn, thread, line, wire, or the like. In this way, the surgeon only needs to pierce the target tissue site with the needle and tie the drug depot to the target tissue site via a knot. This is one embodiment of the drug depot's easy tie system, where surgical steps of threading the needle and depot are eliminated because the needle, suture and depot are pre-threaded.

Shown in FIG. 2 at 18 is a region of the suture that is larger in circumference and/or diameter than the channel of the depot and thus prevents the suture from being pulled through the drug depot. In some embodiments, the needle can pierce the target tissue site first, then the needle and suture can be used to thread the drug depot channel, which acts as a guide for the surgeon or be tied around the drug depot. The surgeon can then can tie the drug depot to the target tissue site and knot and cut the suture to anchor the drug depot at or near the target tissue site.

Figure 2A:
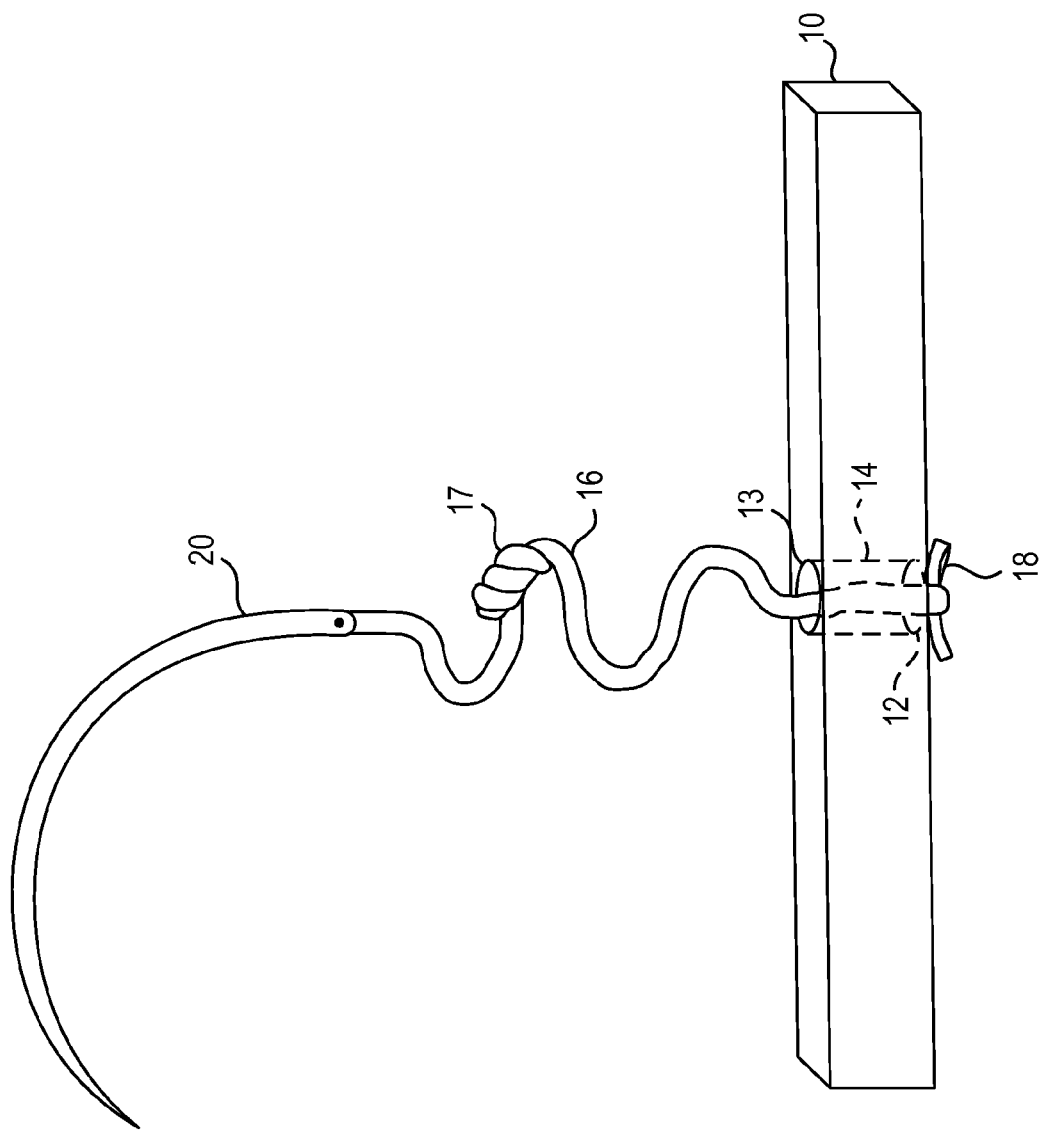
FIG. 2A is a side sectional view of one embodiment of the implantable drug depot showing the pull and cut system. The suture has two regions that are larger (shown as knots) than other regions of the suture. The surgeon uses the needle to pierce the tissue and the surgeon pulls the needle and suture back through the channel to lock the depot in place. The suture can then be cut. In this way, time consuming-steps of tying knots to anchor the depot are avoided.

FIG. 2A is a side sectional view of one embodiment of the implantable drug depot 10. The pull and cut system is illustrated. The drug depot has a surface, in this case a channel 14, disposed in the center of the depot to receive a suture 16 as the anchoring member. The suture in this illustration has two regions 17 and 18 that are pre-knotted. In some embodiments, the suture regions are spaced a distance from each other so as to allow the depot to be sutured and pulled on, in, or through the one or more surfaces (e.g., channels) of the depot. In some embodiments, the depot can be spaced 0.5 mm, 1 mm, 5 mm, 10 mm, 20 mm, 50 mm, 100 mm or 1 cm, 5 cm, or 10 cm apart from each other depending on the depth of the target tissue site.

One of the regions 18 holds the suture in place inside the depot and the other region 17 travels with the needle, when the needle pierces the target tissue site. After piercing the tissue site, the surgeon returns the suture to opening 13 and through channel 14 and out through opening 12. Pulling the suture taut forces knot 17 through opening 12 and locks the suture in place. After pulling, all the surgeon need do is cut the suture adjacent to the exposed knot to implant the depot. In various embodiments, this pull and cut system saves the surgeon time consuming-steps of tying knots to anchor the depot. In some embodiments, since the surgeon has no need to tie knots, the drug depot is suitable for laparoscopic, arthroscopic, neuroendoscopic, endoscopic, rectoscopic procedures or the like.

Although channels are shown on the drug depot surface, it will be understood by one of ordinary skill in the art that any anchoring means may be used to facilitate attachment of the anchoring member to the drug depot. Anchoring means include, for example, grooves, slits, loops, hooks, eyelets, barbs, posts, tabs, clips, or the like can be used in conjunction with or instead of the channels. For example, one or more grooves, slits, loops, hooks, eyelets, barbs, posts, tabs, and/or clips can be disposed on, in or above the top and/or bottom surfaces of the drug depot to facilitates the anchoring member being attached to or through the drug depot (e.g., the surgeon can slip the suture region under a clip, hook, tab, or barb extending from the drug depot to anchor the depot to the target tissue site).

Figure 2B:
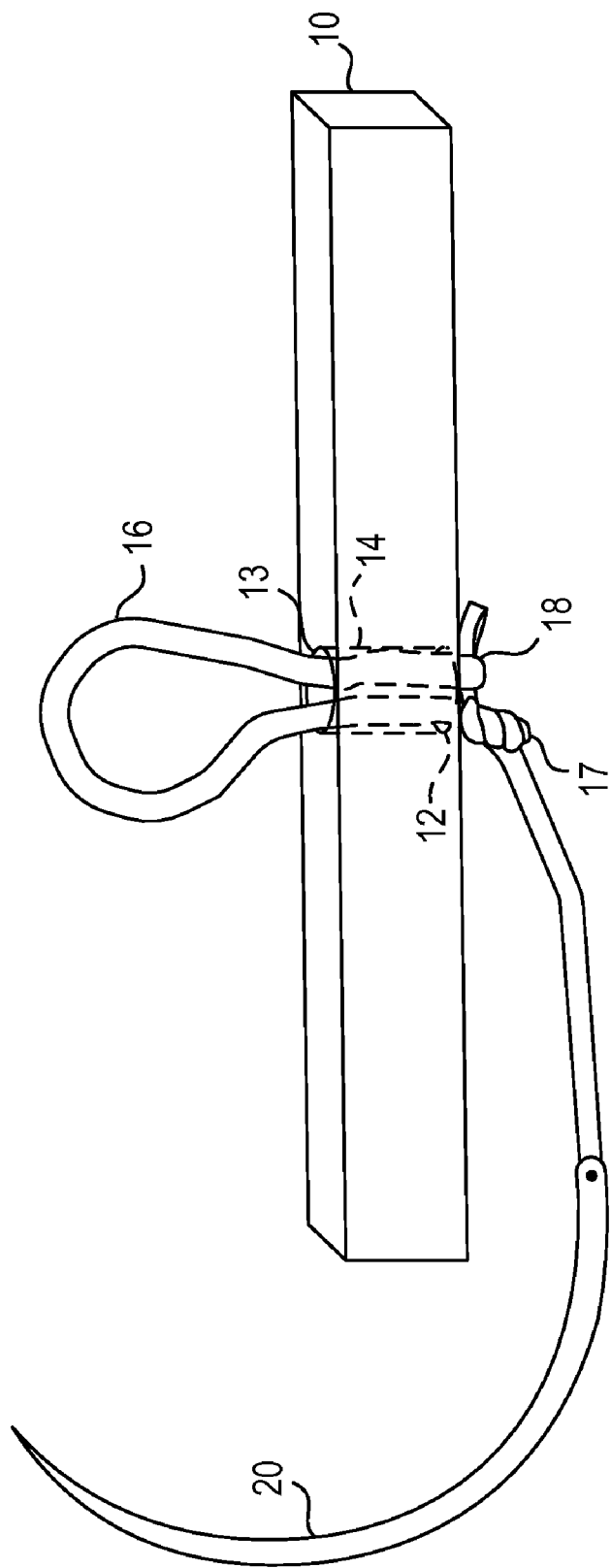
FIG. 2B is a side sectional view of one embodiment of the implantable drug depot showing the suture pulled through the drug depot. Upon implanting the depot, all the surgeon need do is pull the region of the suture through the depot channel to lock it in place and cut the suture.

FIG. 2B is a side sectional view of one embodiment of the implantable drug depot 10. The pull and cut system is illustrated, where the suture is pulled through the depot. The drug depot has a surface, in this case a channel 14, disposed in the center of the depot to receive a suture 16 as the anchoring member. The suture in this illustration has two regions 17 and 18 that are pre-knotted. One of the regions 18 holds the suture in place inside the depot and the other region 17 travels with the needle, when the needle pierces the target tissue site. After piercing the tissue site, the surgeon returns the suture to opening 13 and through channel 14 and out through opening 12. Pulling the suture taut forces knot 17 through opening 12 and locks the suture in place. After pulling, all the surgeon need do is cut the suture adjacent to the exposed knot to implant the depot.

It will also be understood by those of ordinary skill in the art that although the one or more regions of the suture are shown as one or more knots, the suture can have other locking means adapted to hold the suture at different position in the depot. Such locking means disposed along the regions of the suture include, but are not limited to, one or more hooks, barbs, posts, beads, tabs, rims, clips, and/or ridges, or the like that are adapted to hold the suture in position. For example, the suture can have two hooks, barbs, posts, beads, tabs, rims, clips, or ridges that are larger than the channels so that one will hold the suture within the depot and the other the surgeon forces through the channel of the depot by pulling the suture taut to lock the depot at a target tissue site. In some embodiments, these hooks, barbs, posts, beads, tabs, rims, clips, and/or ridges, or the like may be made of biodegradable material as the depot and the suture.

Figure 3:
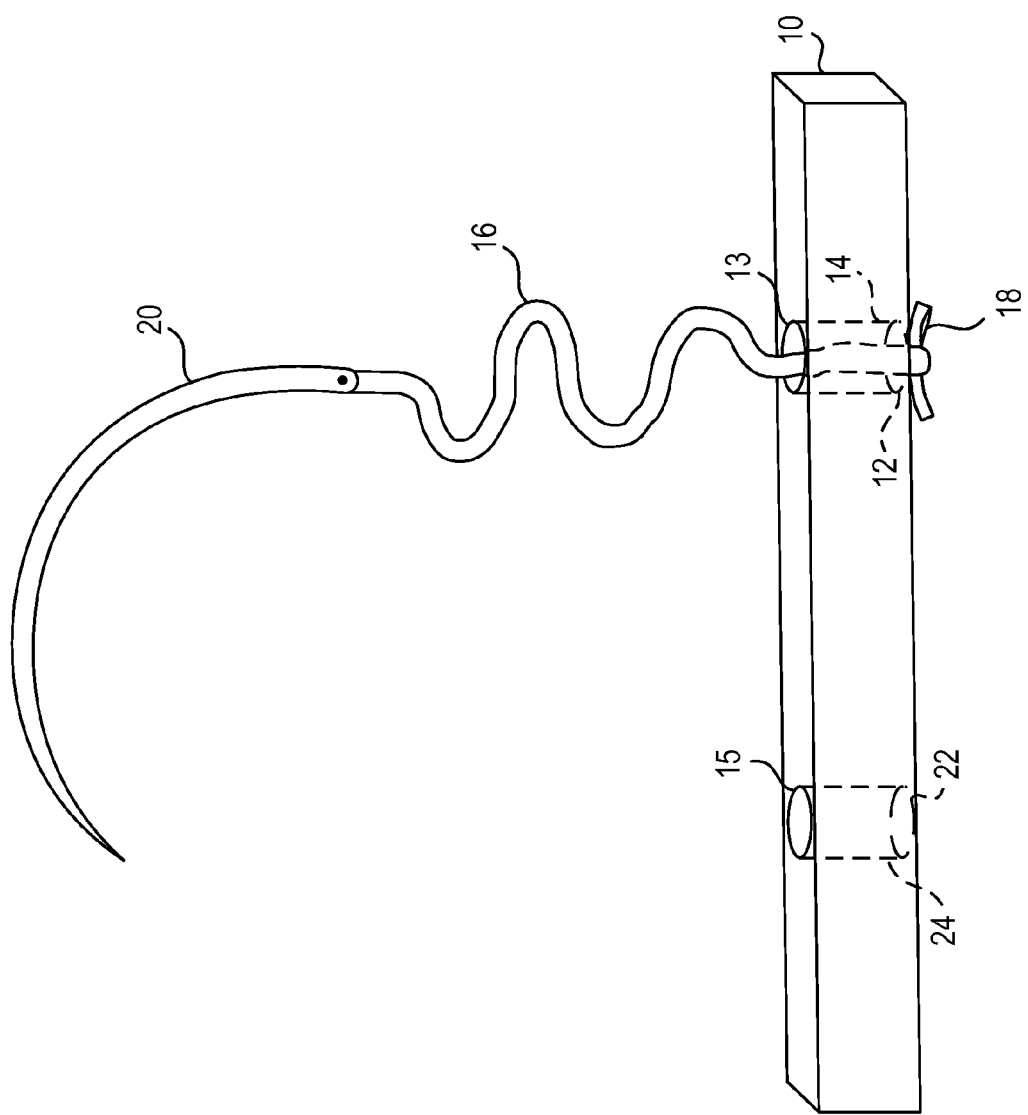
FIG. 3 is a side sectional view of one embodiment of the implantable drug depot having two surfaces, in this case two channels, disposed at different ends of the drug depot that can receive a suture as the anchoring member and allow the drug depot to be sutured at or near a target tissue site.

FIG. 3 is a side sectional view of one embodiment of the implantable drug depot 10 having two surface openings 13 and 15 that lead to two channels at opposite ends shown as 14 and 24, which are adapted to receive a needle 20 having an anchoring member such as a suture 16 attached thereto that is passed through opening 12 through channel 14 and out of opening 13 of the drug depot. This is one example of a pre-threaded drug depot design. The needle and suture extend from the channel, where the needle can pierce a target tissue site and then return to unfilled attachment surface opening 15 and be passed through channel 24 out to opening 22, where the suture can be looped and knotted at, near or against a target tissue.

Shown in FIG. 3 is a knot 18, that the surgeon may tie and then pass the needle and suture through the channel 14 or the knot may be made beforehand when the drug depot is pre-threaded with suture, yarn, thread, line, wire, or the like. In this way, the surgeon only needs to pierce the target tissue site with the needle and then return the needle and suture to unfilled opening 15 and channel 24 will guide the needle and suture through the drug depot out the surface opening 22, where the drug depot can be anchored in place at or near the target tissue site via a knot. This is one embodiment of the drug depot's easy tie system, where surgical steps of threading the needle and depot are eliminated because the needle, suture and depot are pre-threaded.

Shown in FIG. 3 at 18 is a region of the suture that is larger in size (e.g., in circumference and/or diameter) than the channel of the depot and thus prevents the suture from being pulled through the drug depot. In this embodiment, the surgeon uses the needle and suture to pierce the target tissue site and then the same needle and suture is threaded through second opening 15 and second channel 24 acts as a guide to allow the suture out opening 22, where a knot can be tied by the surgeon and the suture can be pulled taut so that the drug depot can be sutured and anchored at or near the target tissue site. As in FIGS. 1 and 2, the openings in the channels have the geometry to allow the anchoring member to pass therethrough.

Figure 4:
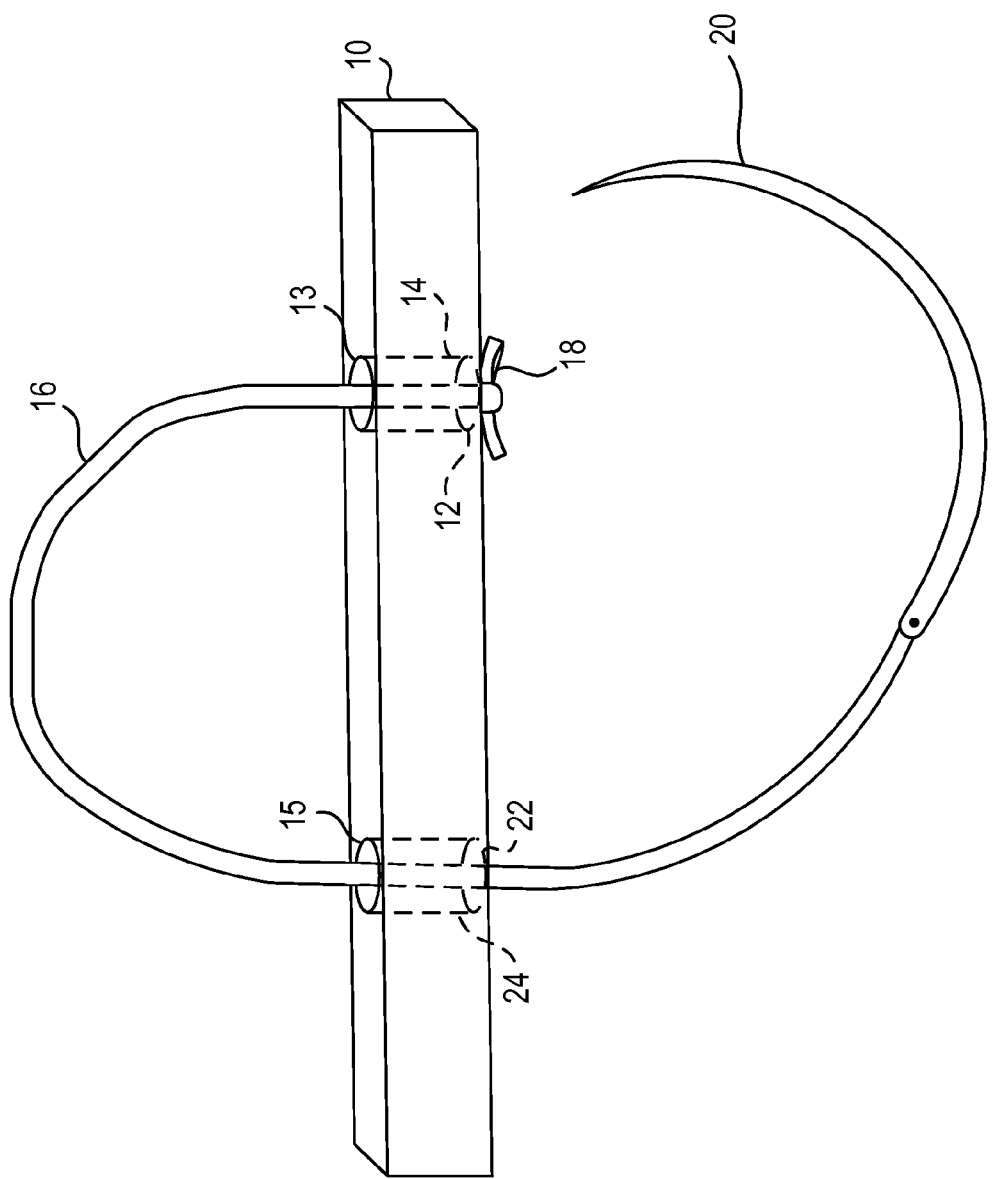
FIG. 4 is a side sectional view of one embodiment of the implantable drug depot having two surfaces, in this case two channels, disposed at different ends of the drug depot that can receive a suture as the anchoring member and allow the drug depot to be sutured at or near a target tissue site. In this view, the same suture is used to anchor the drug depot to the target tissue.

FIG. 4 is a side sectional view of one embodiment of the implantable drug depot 10 having two surface openings 13 and 15 that lead to two channels at opposite ends shown as 14 and 24, which are adapted to receive a needle 20 having an anchoring member such as a suture 16 attached thereto that is passed through opening 12 through channel 14 and out of opening 13 of the drug depot. The needle and suture extend from the channel, where the needle can pierce a target tissue site and then return to attachment surface opening 15 and be passed through channel 24 out to opening 22, where the suture can be looped and knotted at, near or against a target tissue. Shown in FIG. 4 is a knot 18, that the surgeon may tie and then pass the needle and suture through the channel 14 or the knot may be made beforehand when the drug depot is pre-threaded with suture, yarn, thread, line, wire, or the like. In this way, the surgeon only needs to pierce the target tissue site with the needle and then return the needle and suture to unfilled opening 15 and channel 24 will guide the needle and suture through the drug depot out the surface of opening 22, where a knot can be made to anchor the drug depot. This is one embodiment of the drug depot's easy tie system, where there are reduced steps in surgery of pre-threading the needle with the suture and pre-threading the drug depot with the needle. Shown in FIG. 4 at 18 is a region of the suture that is larger in size (e.g., in circumference and/or diameter of the channel of the depot and thus prevents the suture from being pulled through the drug depot. In this embodiment, the surgeon uses the needle and suture to pierce the target tissue site and then the same needle and suture is threaded through second opening 13 and second channel 14 acts as a guide to allow the suture out opening 12, where a knot can be tied by the surgeon and the suture can be pulled taut so that the drug depot can be sutured and anchored at or near the target tissue site.

In some embodiments, the drug depot can be positioned inside the body of a patient under the skin and against a tissue plane, and a needle having the suture is passed through the drug depot surface and then into the anatomical site to anchor the drug depot at or near the target tissue site. After the needle has pierced through a body tissue, the needle and suture are used to thread the drug depot via the second channel and a knot is made and the needle is cut off from the suture according to surgical fastening methods.

In some embodiments, the anchoring member can be a staple and the drug depot surface is adapted to receive the staple or the staple can pierce the drug depot and the target tissue site to anchor the drug depot. For example, the surgeon can place the drug depot against the target tissue site and then staple the drug depot to the target tissue site. In this way the surgeon can easily implant the drug depot.

Figure 4A:
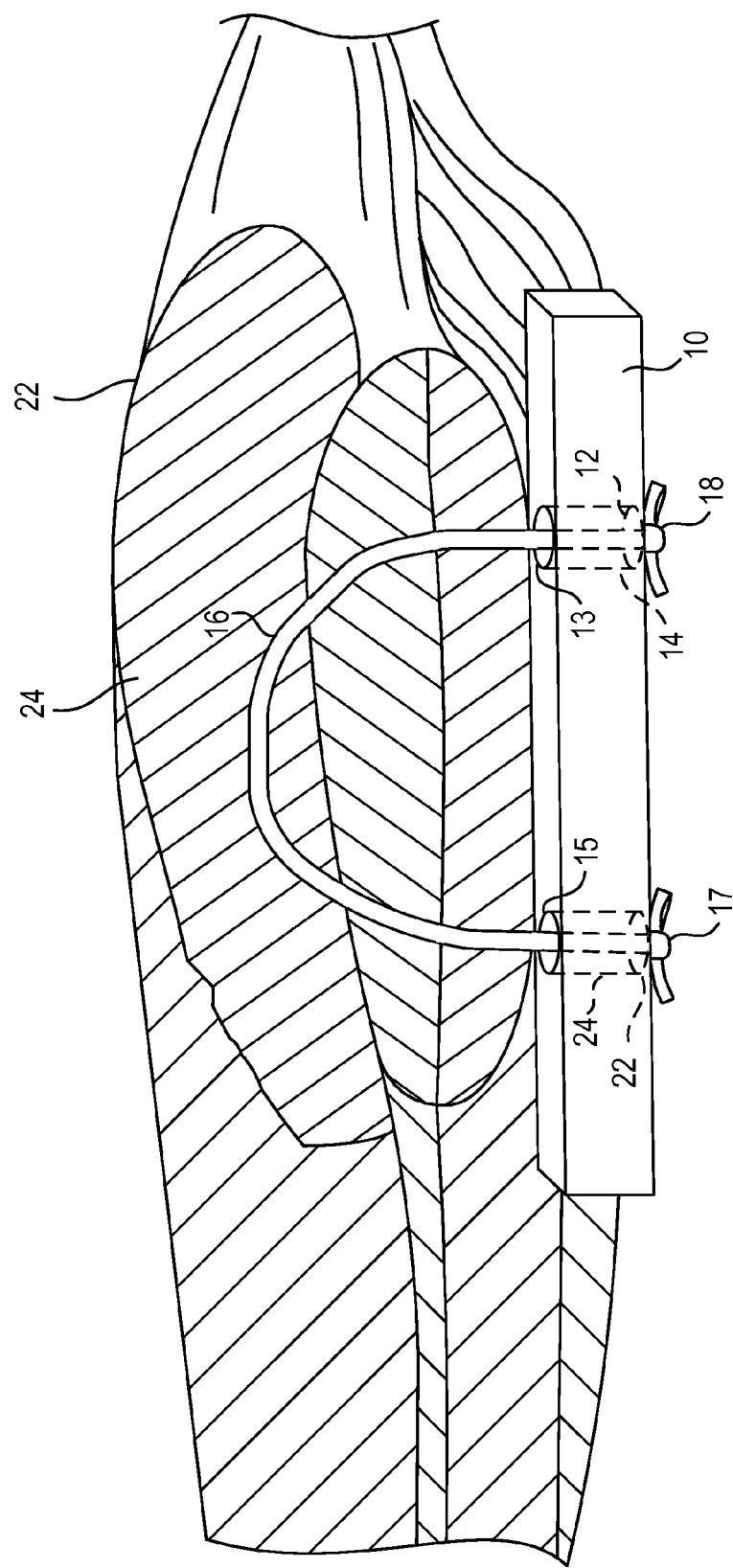
FIG. 4A is an enlarged side sectional view of one embodiment of the implantable drug depot having two surfaces, in this case two channels, disposed at different ends of the drug depot that receive a suture as the anchoring member and allow the drug depot to be sutured at or near a target tissue site. In this view, the same suture is used to anchor the drug depot to a muscle and the surgeon knots the suture to keep the drug depot in place.

FIG. 4A is a side sectional view of one embodiment of the implantable drug depot 10 having two surface openings 13 and 15 that lead to two channels (14 and 24) and openings 22 and 12, which are adapted to receive a needle having an anchoring member such as a suture 16 that is passed through opening 12 through channel 14 and out of opening 13 of the drug depot. The needle and suture extend from the channel, where the needle can pierce a target tissue site beneath the skin 22. In this case, the target tissue site comprises muscles tissue 24. The needle and suture pierce the muscle tissue and then return to attachment surface at the other end of the depot opening 15 and is guided through channel 24 out to opening 22, where the suture can be looped and knotted at, near or against a target tissue. Shown in FIG. 4A is a bead 18 that is used to pre-attach the suture to one end of the drug depot. This bead is attached to a region of the suture and is larger than the channel and opening so that the surgeon cannot pull this end of the suture out of the drug depot. After the surgeon pierces the muscle tissue 24 with the needle, the surgeon brings the needle and suture back through second opening 15 and the needle and suture are guided through channel 24 out opening 22 and the surgeon knots the suture and cuts the needle and suture to anchor the drug depot at or near the target tissue site.

In the embodiment shown in FIG. 4A, the drug depot can be biodegradable and as the drug depot degrades, drug is released at the target tissue site and unwanted migration and consistent drug therapy is provided at or near the target tissue site. In various embodiments, the suture 16 degrades faster than the drug depot so that as the target tissue site heals, the suture will degrade leaving the drug depot lodged deep within the target tissue site to release drug as bodily fluid contacts the drug depot and causes it to degrade over time.

In some embodiments, the suture is pre-attached to the surgical needle and the suture is pre-threaded through or pre-attached to the one or more channels, slits, loops, and/or clips or is pre-tied around or pre-attached to the one or more grooves, hooks, barbs, posts and/or clips so as to eliminate some surgical steps and reduce the length of time during surgery.

Figure 5:
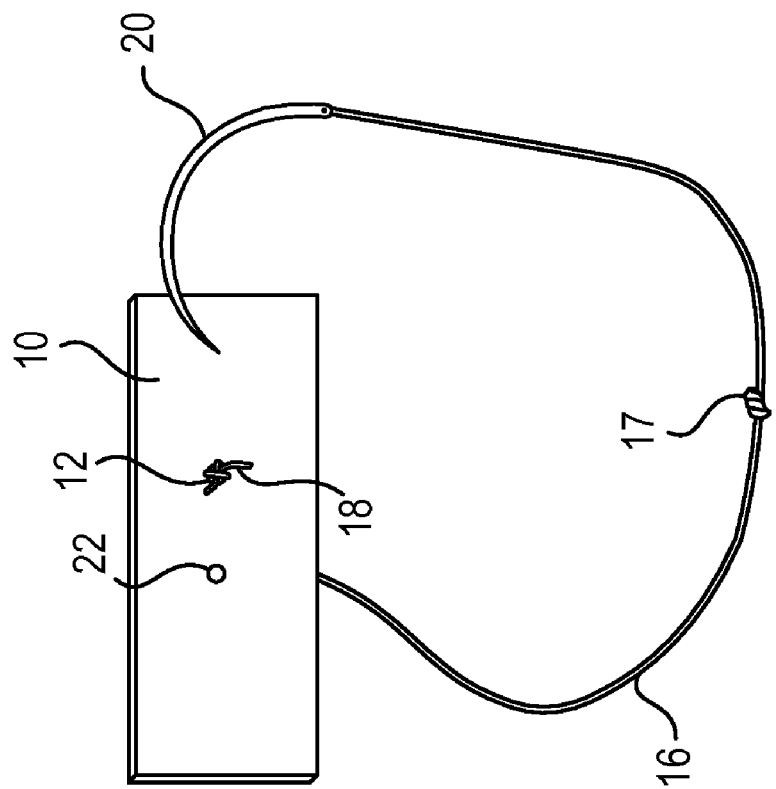
FIG. 5 is a side view of one embodiment of the implantable drug depot having two surfaces, in this case two channels, disposed at different ends of the drug depot that can receive a suture. The suture has two regions, one to hold the suture in place in the depot and the other the surgeon pulls through the channel to lock the depot in place at or near a target tissue site. All the surgeon need do after pulling the suture through the channel is cut the suture. In this way, time-consuming steps of tying knots to anchor the depot are avoided.

FIG. 5 is a side view of one embodiment of the implantable drug depot 10 having two surfaces, in this case two channels openings shown as 12 and 22, disposed at different ends of the drug depot that can receive a suture 16. The suture has two regions, one region 18 to hold the suture in place in the depot and the other region 17 (after piercing the body tissue with needle 20) the surgeon pulls through the channel opening 22 to force region 17 through the opening and lock the depot in place at or near a target tissue site. This illustration shows the depot pre-threaded and pre-knotted (17 and 18). All the surgeon need do after pulling the suture through the channel is cut the suture. This "pull and cut" system avoids time-consuming steps of tying knots to anchor the depot during surgery.

FIG. 5A is a side view of one embodiment of the implantable drug depot 10 having two surfaces, in this case two channels openings shown as 12 and 22, disposed at different ends of the drug depot that can receive a suture 16. The suture has two regions, one region 18 to hold the suture in place in the depot and the other region 17 (after piercing the body tissue with needle 20) the surgeon pulls through the channel opening 22 to force region 17 through the opening and lock the depot in place at or near a target tissue site. This illustration shows the depot pre-threaded and pre-knotted (17 and 18) and suture needle 20 passing through channel opening 22. All the surgeon need do after pulling the suture through the channel is cut the suture.

Figure 5B:
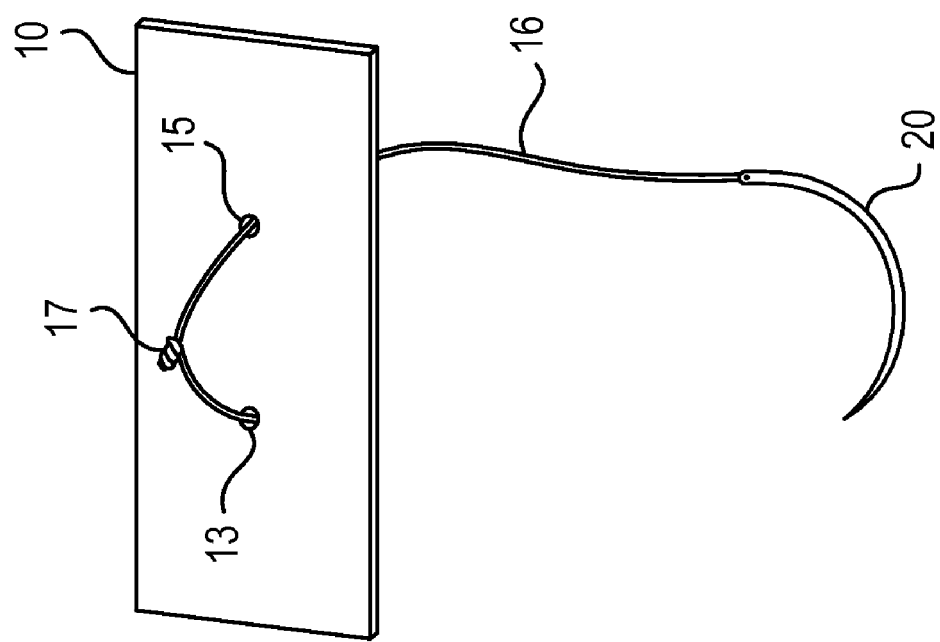
FIG. 5B, 5C and 5D illustrate back views of one embodiment of the implantable drug depot as the suture and needle pass through the second channel. The surgeon pulls the suture through the channel to lock the depot in place at or near a target tissue site. This back part of the depot is implanted against the tissue plane.
Figure 5C:
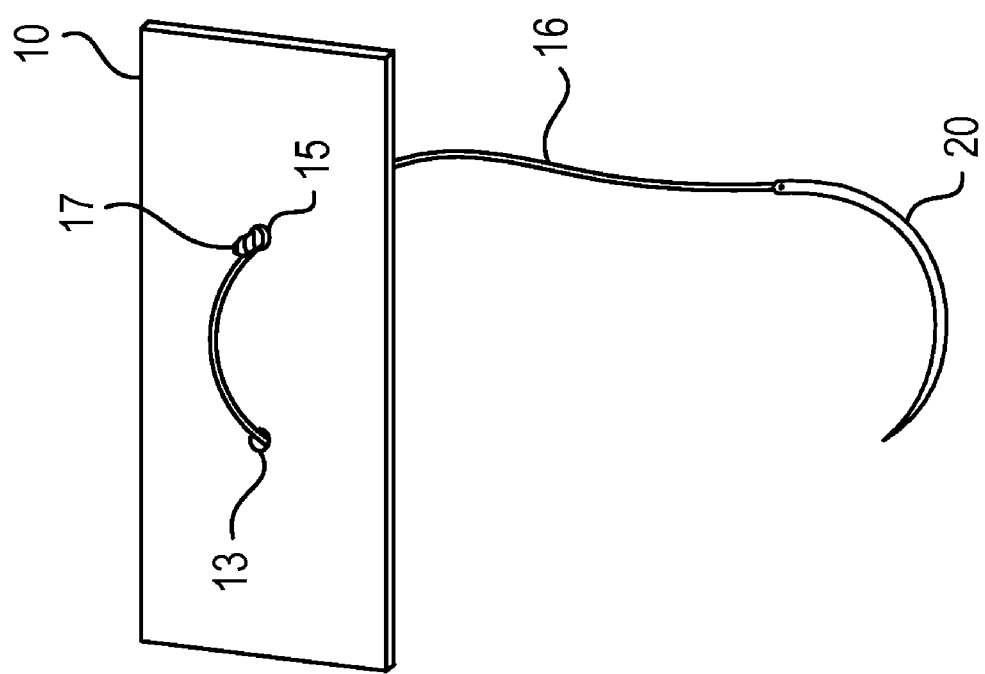
Figure 5D:
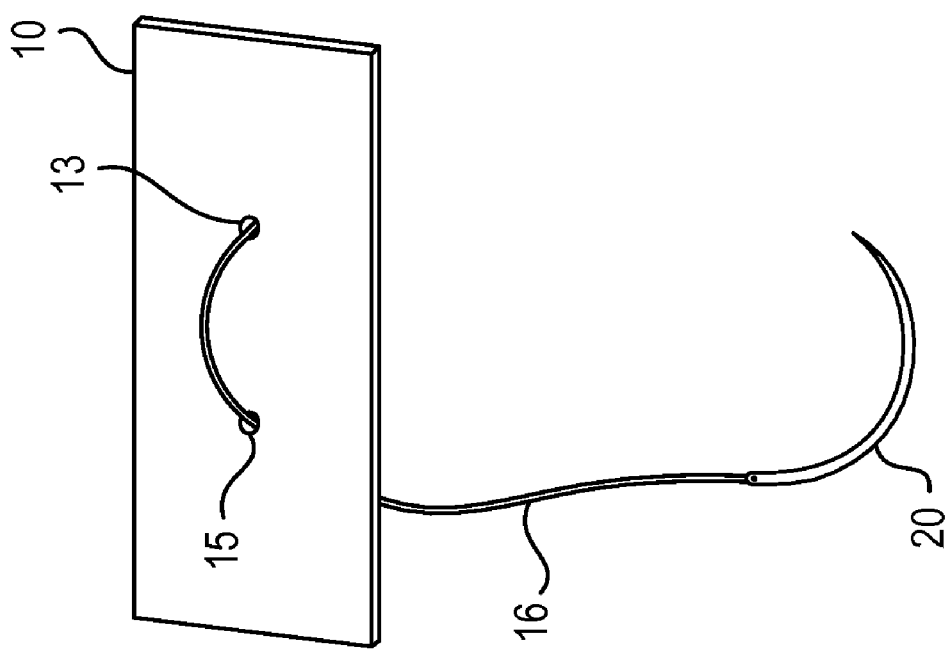

FIGS. 5B, 5C and 5D illustrate back views of one embodiment of the implantable drug depot 10 as the suture 16 and needle 20 pass through the channel opening 13. The suture has a region 17 (after piercing the body tissue) that the surgeon pulls and forces it through opening 15 and locks the depot in place at or near a target tissue site. This illustration shows the depot pre-threaded and pre-knotted and suture needle passed through channel opening 15 and region 17 about to be pulled through (FIGS. 5B and 5C). FIG. 5D shows the suture 16 and needle 20 pulled through the channel opening 15 of the drug depot 10. This back part of the depot, in some embodiments, is implanted against the tissue plane.

Figure 5E:
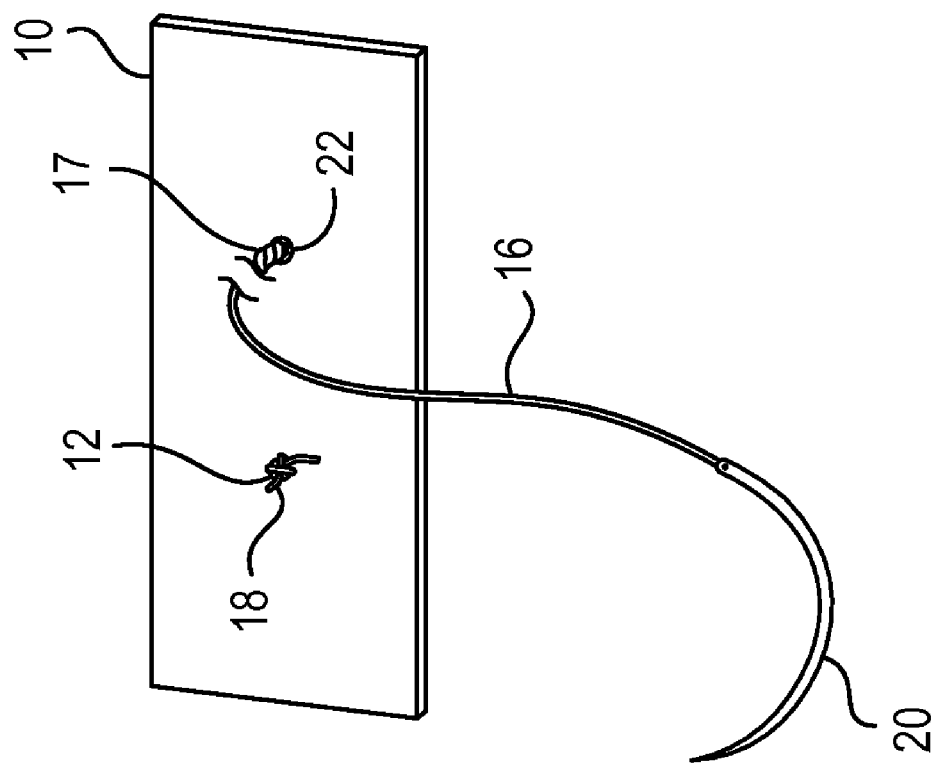
FIG. 5E illustrates a front view of one embodiment of the implantable drug depot as the surgeon pulls the suture through the channel to lock the depot in place. After pulling, all the surgeon need do is cut the suture.

FIG. 5E illustrates a front view of one embodiment of the implantable drug depot 10 having two surfaces, in this case two channels openings shown as 12 and 22, disposed at different ends of the drug depot that receive a suture 16. The suture has two regions, one region 18 to hold the suture in place in the depot and the other region 17 (after piercing the body tissue with needle 20) the surgeon pulls through the channel opening 22 to force region 17 through the opening and lock the depot in place at or near a target tissue site. This illustration shows the depot pre-threaded and pre-knotted (17 and 18) and the suture being cut adjacent to knot 17.

Figure 5F:
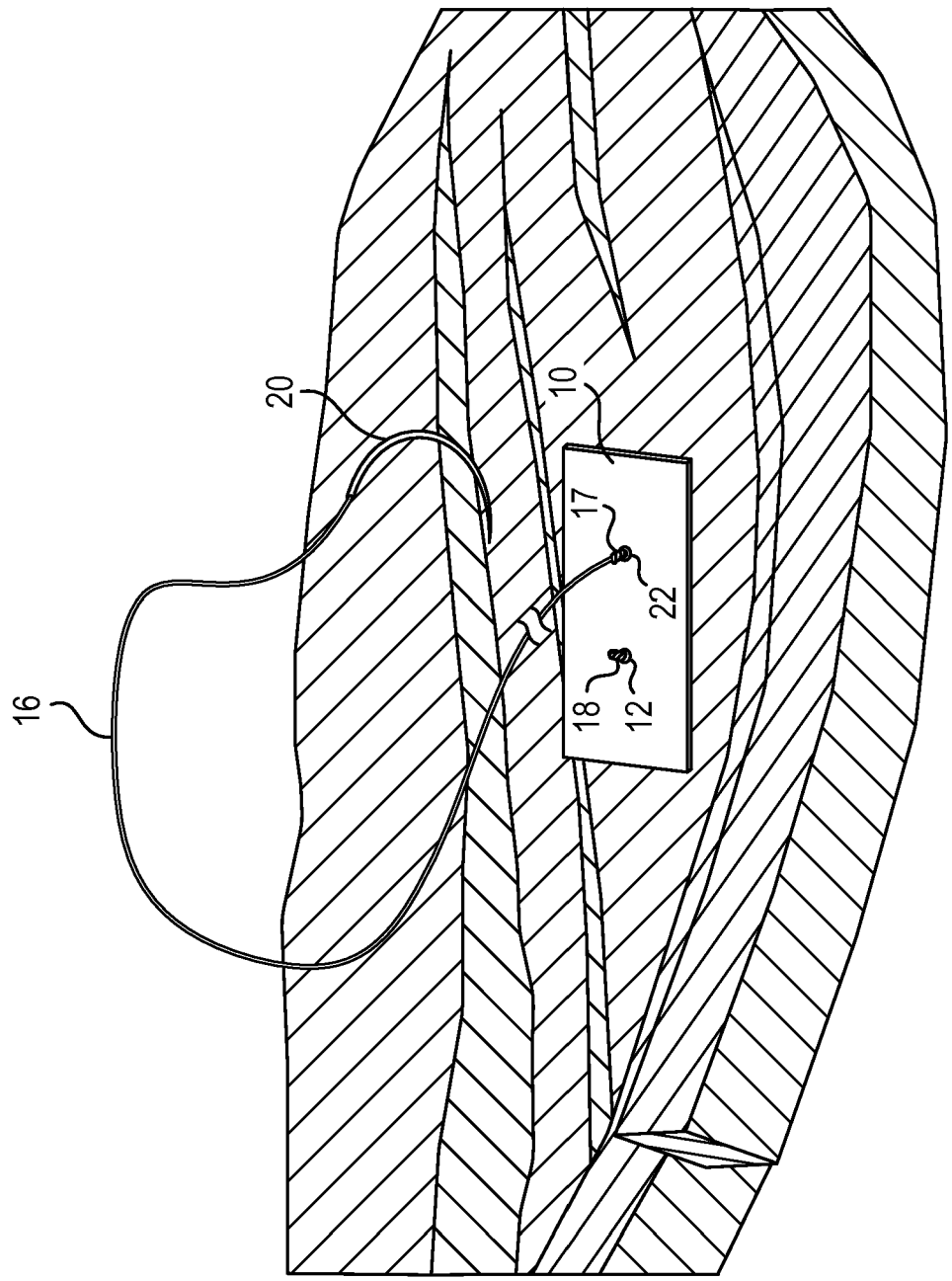
FIG. 5F illustrates a front view of one embodiment of the drug depot implanted at a target tissue site.
Figure 5G:
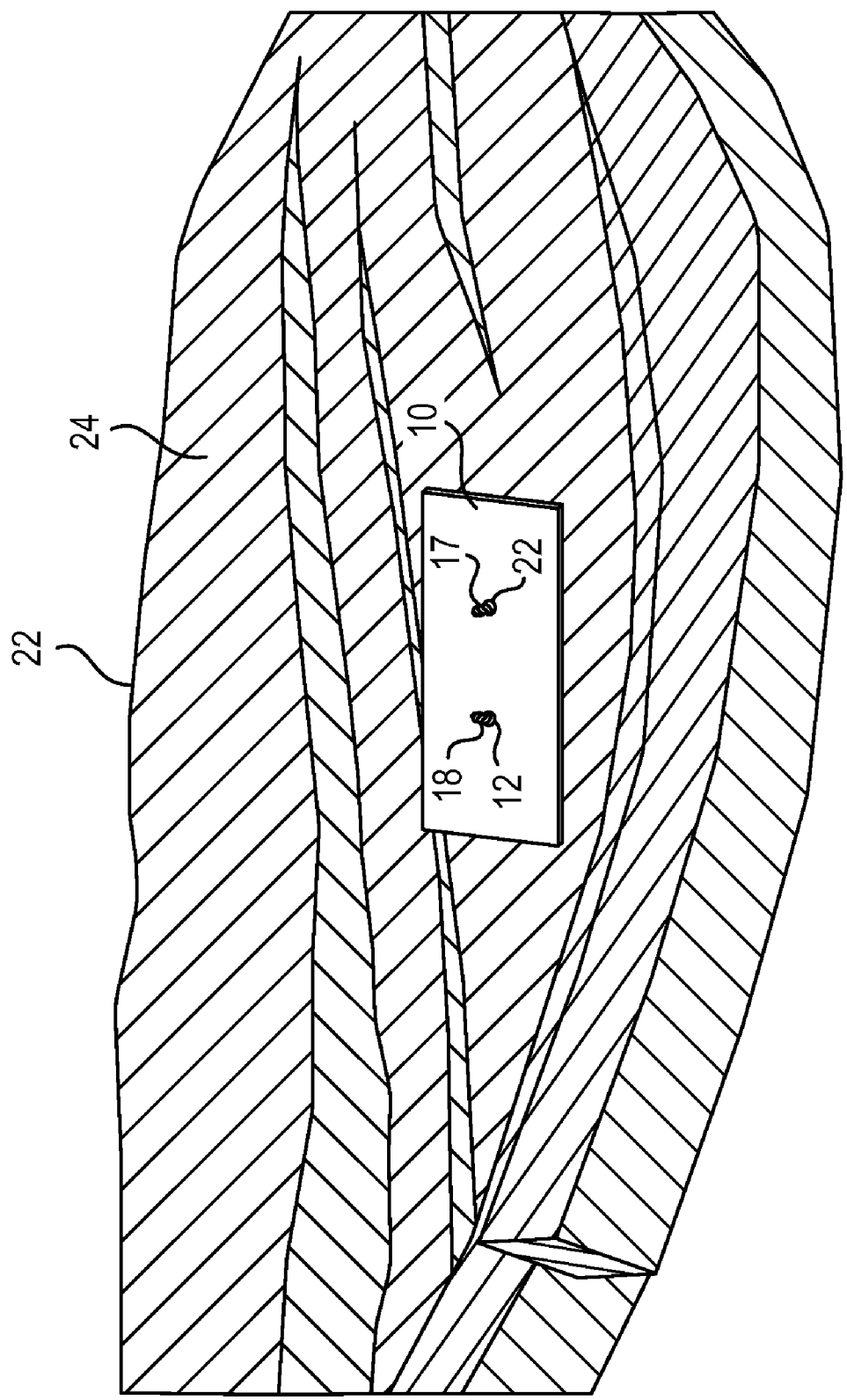
FIG. 5G illustrates a front view of one embodiment of the drug depot. This view shows the suture cut and the drug depot implanted at a target tissue site.

FIGS. 5F and 5G illustrate a front view of one embodiment of the drug depot 10 implanted at a target tissue site (muscle 24 in FIG. 5G) beneath the skin (22 in FIG. 5G). The drug depot has two surfaces, in this case two channels openings shown as 12 and 22, disposed at different ends of the drug depot that receive a suture 16. The suture has two regions, one region 18 to hold the suture in place in the depot and the other region 17 (after piercing the body tissue with needle 20) the surgeon pulls through the channel opening 22 to force region 17 through the opening and lock the depot in place at or near a target tissue site. The illustration in FIG. 5F shows the depot pre-threaded and pre-knotted (17 and 18) and implanted and the suture being cut adjacent to knot 17. FIG. 5G illustrates the depot implanted after excess suture and the needle are removed.

It will be understood by one of ordinary skill in the art that the depot may have the holes, channels, grooves, slits, or the like pre-made in it that is done by the manufacturer. Alternatively, the holes, channels, grooves, slits, or the like can be made by the user using the needle.

In some embodiments, the holes, channels, grooves, slits, or the like can be made by punching, drilling, laser, or the like. The suture and needle can be attached by hand or automated machine. Suture knots can be created by hand or automated machine. Other capture means or mechanisms (channels, holes, ports, grooves, slits, loops, hooks, barbs, posts, beads, tabs, and/or clips) can be pre-molded into depot implant shape, machined in, or attached secondarily.

It will be understood by one of ordinary skill in the art that although the at least one surface is shown as a channel in FIGS. 1-5G, the surface of the drug depot can be one or more grooves, slits, loops, hooks, eyelets, barbs, posts or the like as long as the surface facilitates the anchoring member being attached to or through the drug depot. The at least one attachment surface of the drug depot, in various embodiments, may extend from the body of the drug depot, such as for example, in a channel, loop, hook, eyelet, barb, post, structure or the like.

In some embodiments, the one or more channels, grooves, slits, loops, hooks, eyelets, barbs, posts and/or clips of the drug depot may be spaced apart equidistant from each other. For example, the one or more channels, grooves, slits, loops, hooks, eyelets, barbs, posts and/or clips may be spaced apart by 0.5 mm, 1 mm, 5 mm, 10 mm, 20 mm from each other.

Figure 6A:
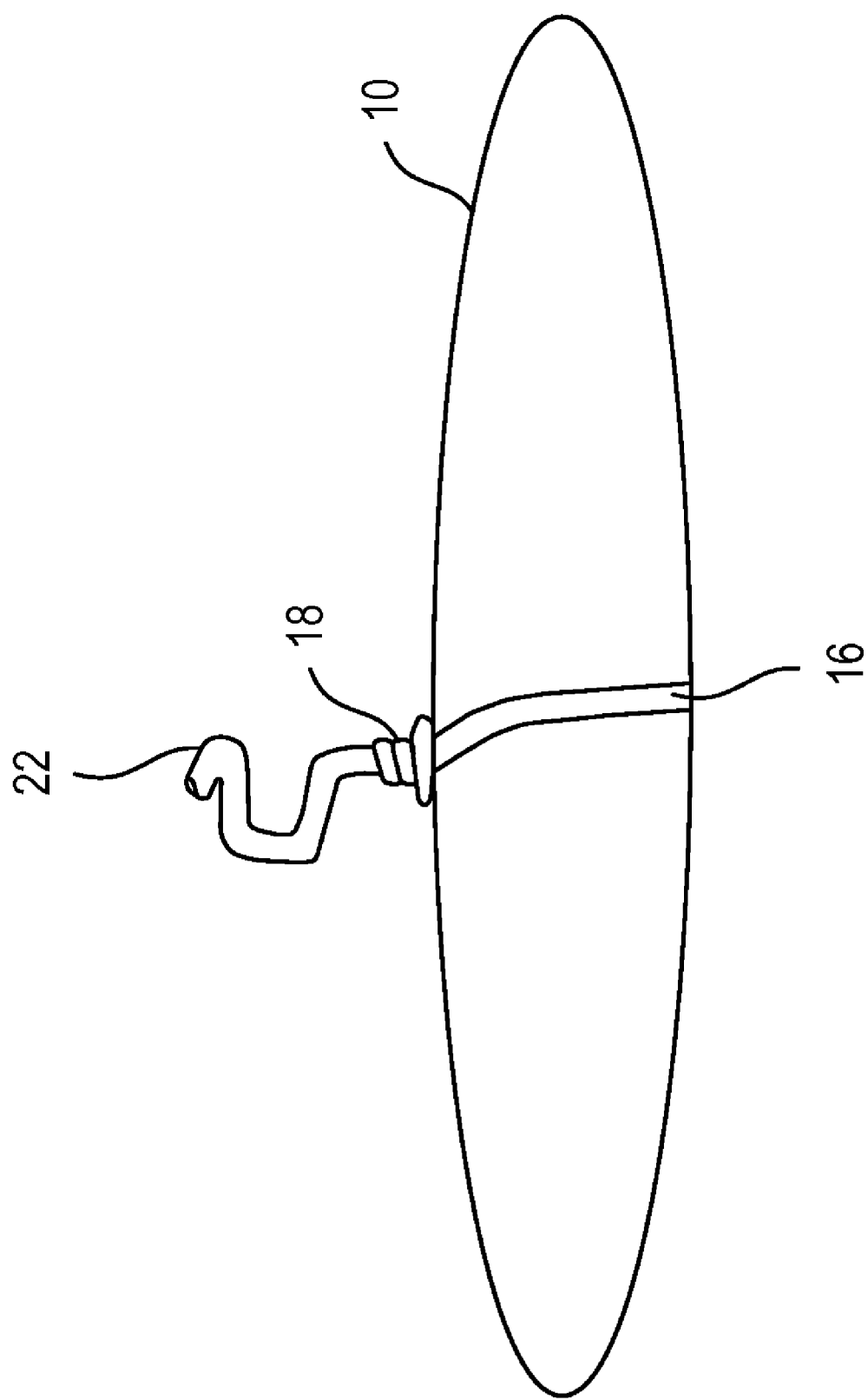
FIG. 6A is a side view of one embodiment of the implantable drug depot having a surface adapted to receive a suture, where the surgeon can tie the suture to the depot at one end and suture the other end of the depot at or near a target tissue site.

FIG. 6A is a side view of one embodiment of the implantable drug depot 10 having a surface adapted to receive a suture 16, where the surgeon can tie the suture to the depot shown as a knot 18 at one end and the other end 22 of the suture can be attached to a needle, which is used to pierce the target tissue site and the suture end 22 can be tied in a knot and the needle cut and removed. In this way, the drug depot can be anchored at or near the target tissue.

Figure 6B:
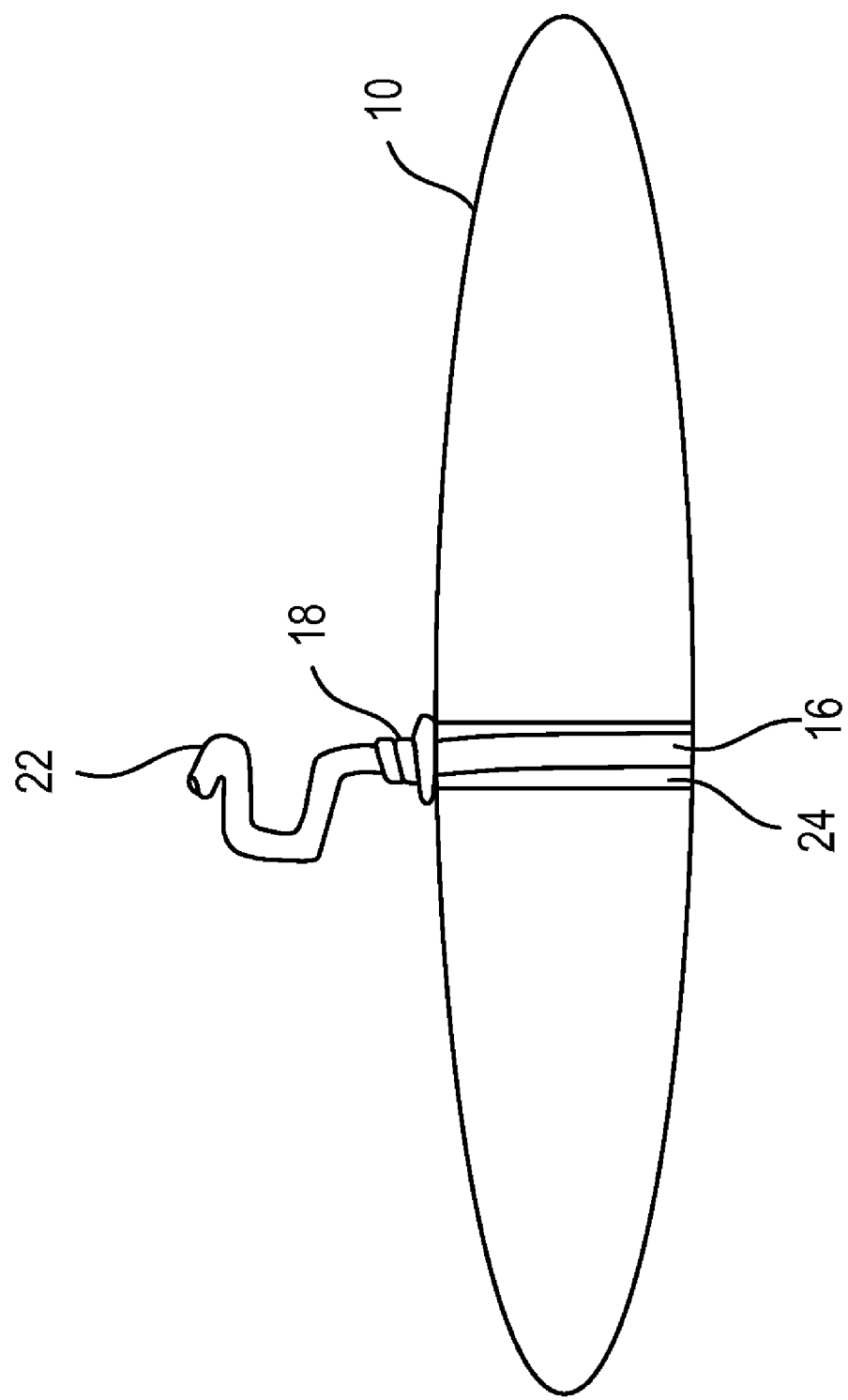
FIG. 6B is a side view of one embodiment of the implantable drug depot having a surface adapted to receive a suture, in this case a groove, where the surgeon can tie one end of the suture to the depot and use the other end of the suture to anchor the depot at or near a target tissue site.

FIG. 6B is a side view of one embodiment of the implantable drug depot 10 having a surface, in this case a groove 24 running around the circumference of the drug depot, adapted to receive a suture 16 where the suture can be tied 18 around groove 24 and one end of the suture 22 can be threaded through a needle. The needle and suture can pierce the target tissue site and the needle and suture returned and the suture knotted and the needle cut and removed. In this way, the drug depot can be sutured at or near the target tissue site. In various embodiments, the drug depot can have the suture pre-attached to the drug depot saving the surgeon surgical steps and time in threading the needle and the drug depot.

Radiographic markers can be included on the drug depot to permit the user to position the depot accurately into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging, fluoroscopy, or MRI. Examples of such radiographic markers include, but are not limited to, barium, calcium phosphate, and/or metal beads or particles. In various embodiments, the radiographic marker could be a spherical shape, a line(s), or a ring around the depot.

In some embodiments, the drug depot may have an initial burst effect to release the drug shortly after it is implanted. Various factors can be adjusted to achieve the initial burst of therapeutic agent release. First, the initial burst can be controlled by factors related to the property of the depot, such as the water immiscibility of the solvent, polymer/solvent ratio, and the property of the polymer. The extent of water immiscibility of the solvent used in the depot affects that rate aqueous body fluid can penetrate the depot to release the therapeutic agent. Generally, higher water solubility leads to a higher initial burst while water immiscibility leads to a lower initial burst or slower release (sustained release) of the therapeutic agent.

Suitable solvents that can be used to control initial burst release or sustained release include, but are not limited to, methyl benzoate, ethyl benzoate, n-propyl benzoate, isopropyl benzoate, butyl benzoate, isobutyl benzoate, sec-butyl benzoate, tert-butyl benzoate, isoamyl benzoate, benzyl benzoate, water, alcohol, low molecular weight PEG (less than 1,000 MW), triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, mineral oil, polybutene, silicone fluid, glycerin, ethylene glycol, octanol, ethyl lactate, propylene glycol, propylene carbonate, ethylene carbonate, butyrolactone, ethylene oxide, propylene oxide, N-methyl-2-pyrrolidone, 2-pyrrolidone, glycerol formal, methyl acetate, ethyl acetate, methyl ethyl ketone, dimethylformamide, glycofurol, dimethyl sulfoxide, tetrahydrofuran, caprolactam, decylmethylsulfoxide, oleic acid, 1-dodecylazacyclo-heptan-2-one, or mixtures thereof. The solvent can be mixed, in various embodiments, with the therapeutic agent and/or polymers to obtain the desired release profile.

The depot may have pore forming agents, which include biocompatible materials that when contacted with body fluids dissolve, disperse or degrade to create pores or channels in the polymer matrix. Typically, organic and non-organic materials that are water soluble such as sugars (e.g., sucrose, dextrose), water soluble salts (e.g., sodium chloride, sodium phosphate, potassium chloride, and sodium carbonate), water soluble solvents such as N-methyl-2-pyrrolidone and polyethylene glycol and water soluble polymers (e.g., carboxymethylcellulose, hydroxypropyl-cellulose, and the like) can conveniently be used as pore formers. Such materials may be present in amounts varying from about 0.1% to about 100% of the weight of the polymer, but will typically be less than 50% and more typically less than 10-20% of the weight of polymer.

Further, varying the molecular weight of the polymer in the depot, or adjusting the molecular weight distribution of the polymer material in the depot vehicle can affect the initial burst and the release rate of therapeutic agent from the depot. Generally, a higher molecular weight polymer renders a lower initial burst and slower release rate of the therapeutic agent. The polymers may have different end groups such as acid and ester end groups. As persons of ordinary skill in the art are aware, implantable elastomeric depot compositions having a blend of polymers with different end groups are used the resulting formulation will have a lower burst index and a regulated duration of delivery. For example, one may use polymers with acid (e.g., carboxylic acid) and ester end groups (e.g., methyl of ethyl ester end groups).

Additionally, by varying the comonomer ratio of the various monomers that form a polymer (e.g., the LIG (lactic acid/glycolic acid) or G/CL (glycolic acid/polycaprolactone) ratio for a given polymer) there will be a resulting depot composition having a regulated burst index and duration of delivery. For example, a depot composition having a polymer with a LUG ratio of 50:50 may have a short duration of delivery ranging from about two days to about one month; a depot composition having a polymer with a LIG ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a LIG ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery. Thus, among other things, depot compositions having a blend of polymers having different molecular weights, end groups and comonomer ratios can be used to create a depot formulation having a lower burst index and a regulated duration of delivery.

Factors such as the particle size, the disintegration of the particulates, the morphology of the particulates (e.g., whether pores are present in the particulates before implanting or can be formed easily by body fluid attack), coatings, complex formation by the therapeutic agent and the strength of complex bond, can be manipulated to achieve the desired low initial burst and release rate.

Suture

Suture may be resorbable or permanent in nature depending upon the type of material from which it is made. As used herein, "suture" refers to any flexible structure that can be stretched between two points and includes, without limitation, traditional suture material, single or multiple stranded threads, or a mesh structure. A suture may also be a strap-like structure with a number of holes in it, similar to the holes found in a belt. A "suture" may also take the form of an acellular, collagen membrane or other biologic tissue augment, which may provide a scaffold or support matrix for cellular ingrowth to allow soft tissue to reconstruct itself. Sutures for attachment to surgical needle include silk, nylon, linen, cotton, chromic gut, plain gut, cat gut, vicryl, polyglactin, polyester, polypropylene, stainless steel, synthetic polymers having glycolic acid ester linkages subject to hydrolytic degradation to non-toxic tissue compatible absorbable components, including polyglycolic acid. The sutures may be monofilamentary or braided, absorbable or non-absorbable. The suture may be of any length. In various embodiments, the suture is long enough to reach from the site of placement of the depot to the target tissue site. The suture may be of any thickness provided it can be attached to or pass through the drug depot. In some embodiments, the suture may be coated with a drug.

A variety of bioabsorbable polymers can be used to make the suture. Examples of suitable biocompatible, bioabsorbable polymers include aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) or blends thereof. Polyesters include, but are not limited to, homopolymers and copolymers of lactide (which includes lactic acid, D-,L- and meso lactide), glycolide (including glycolic acid), caprolactone, p-dioxanone (1,4-dioxan-2-one), trimethylene carbonate (1,3-dioxan-2-one), alkyl derivatives of trimethylene carbonate, delta-valerolactone, beta-butyrolactone, gamma-butyrolactone, epsilon-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one 2,5-diketomorpholine, pivalolactone, alpha-diethylpropiolactone, ethylene carbonate, ethylene oxalate, 3-methyl-1,4-dioxane-2, 5-dione, 3,3-diethyl-1,4-dioxan-2,5-dione, 6,8-dioxabicycloctane-7-one or polymer blends thereof.

In some embodiments, the suture can comprise shape memory polymers including various polyethers, polyacrylates, polyamides, polysiloxanes, polyurethanes, polyether amides, polyurethane/ureas, polyether esters, or urethane/butadiene copolymers or a combination thereof.

In some embodiments, the suture degrades faster than the drug depot. In some embodiments, the drug depot degrades faster than the suture.

Sutures may be of different sizes depending on the procedure being performed and the implant site. Sutures can range in size from #000000 (#6-0 or #6/0), #00 (#2-0 or #2/0), #0, #1, #2, #3, #4, #5, #6, with #000000 being the smallest. In various embodiments, the drug depot will have one or more channels, grooves, slits, loops, hooks, and/or barbs that will be larger than #000000, #00, #0, #1, #2, #3, #4, #5, or #6, range so that the suture can pass through the surface of the drug depot.

Needle

In some embodiments, the one or more channels, grooves, slits, loops, hooks, eyelets, barbs, posts and/or clips are such a size that allows a needle having a suture, yarn, thread, or line pass and be guided through or around the depot. Thus, the one or more channels, grooves, slits, loops, hooks, eyelets, barbs, posts and/or clips may be larger than the needle width and/or thickness and act as a guide for the surgeon to pass the needle therethrough.

The dimensions of the needle, among other things, will depend on the site for implantation. For example, the width of the muscle planes in different surgical procedures can vary from 1-40 cm. Thus, the needle, in various embodiments, can be designed for these specific areas.

Needles may have different shapes such as for example half curved or ski shaped, ¼ circle, ⅜ circle, ½ circle, ⅝ circle, compound curve or the like. Thus, in some embodiments, the drug depot surfaces will be designed to receive the needle and suture so that the needle and suture can pass through the drug depot or allow the suture to be tied around it.

The thickness of the needle will also depend on the site of implantation. In various embodiments, the thickness includes, but is not limited to, from about 0.05 to about 1.655. The gauge of the needle may be the widest or smallest diameter or a diameter in between for insertion into a human or animal body. The widest diameter is typically about 14 gauge, while the smallest diameter is about 25 gauge. In various embodiments the gauge of the needle or cannula is about 18 to about 22 gauge.

Again the one or more channels, grooves, slits, loops, hooks, eyelets, barbs, posts and/or clips may have a size larger than this so the needle having the suture can pass through it. After the needle is pierced through the depot and target body tissue, a knot can be made and the needle is cut off from the suture according to surgical fastening methods.

Suturing needles for applying sutures, or stitches, by hand or via an automated device, such as for example in arthroscopic surgeries can be used in the present application. Suturing needles are usually made from a cut blank of material, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The needle may optionally include one or more tapered regions. In various embodiments, the needle generally includes a shaft, a rear end portion with an aperture or channel to secure a suture thread and a needle head at a front end portion for puncturing skin and passing through tissue. The needle head typically incorporates a sharpened needle tip at its distal end and cutting edges. Alternatively, the needle tip may be of a tapered configuration. Straight and curved needles including multiple curved configurations are also known in the art. Suture needles typically incorporate a sharpened needle end. Sharper needles require less force to penetrate tissue and thus cause less tissue trauma. In addition, a sharper needle reduces fatigue on the needle itself, making it less likely to bend or break during suturing. Needle sharpness is typically defined in terms of "penetration force"—the force necessary for a needle to puncture, or penetrate, the tissue. The penetration force is primarily determined by the design and sharpness of the needle point and the cutting edges formed on the needle head. Needle sharpness is also affected by drag force on the needle as it travels through the tissue. The drag force also depends upon the design and sharpness of the needle, and the presence of a lubricating coating. The choice of materials of surgical needle is made to optimize strength, ductility and resistance to bending or breaking of the needle. However, the cross-sectional shape and dimensions of the needle contributes significantly to the physical characteristics of the needle. In various embodiments, the needle includes stainless steel such as series "300" stainless steels, which typically have tensile strengths of between 325,000-350,000 lbs/in$^2$. When the suture needle is metal such as, for example, stainless steal, the needle cam be manufactured through conventional cutting, coining, grinding and/or swaging processes, and may be heat treated to further enhance its strength and resistance to bending. A lubricious coating such as silicon may be applied to needle body to further enhance penetration and drag characteristics.

Sterilization

The drug depot, medical device to administer the drug, and/or anchoring members (e.g., suture) may be sterilizable. In various embodiments, one or more components of the drug depot, medical device to administer the drug, and/or anchoring members (e.g., suture) may be sterilizable by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In some embodiments, the suture, depot and needle is pre-assembled, packaged in a moisture resistant package and then terminally sterilized by gamma irradiation. In use the surgeon removes the pre-assembled drug depot from the sterile package for use.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the depot and/or one or more components of the device, including, but not limited to, gas sterilization, such as, for example, with ethylene oxide or steam sterilization.

Kits

In various embodiments, a kit is provided comprising one or more drug depots having surfaces adapted to receive one or more anchoring members. The kit may include additional parts along with the drug depot and/or medical device combined together to be used to implant the drug depots (e.g., pellets, strips, meshes etc.). The kit may include the drug depot device in a first compartment. The second compartment may include a canister holding the drug depots or each drug depot with a different release profile may be labeled and placed in a different compartment (e.g., bolus dose depot compartment, sustained release depot compartment, etc.) and any other instruments needed for the localized drug delivery. A third compartment may include gloves, drapes, wound dressings and other procedural supplies for maintaining sterility of the implanting process, as well as an instruction booklet. A fourth compartment may include additional needles and/or sutures. Each tool may be separately packaged in a plastic pouch that is radiation sterilized. A fifth compartment may include an agent for radiographic imaging. A cover of the kit may include illustrations of the implanting procedure and a clear plastic cover may be placed over the compartments to maintain sterility.

Administration

In various embodiments, the drug depot may be parenterally administered. The term "parenteral" as used herein refers to modes of administration, which bypass the gastrointestinal tract, and include for example, intramuscular, intraperitoneal, intrasternal, subcutaneous, intra-operatively, intrathecally, intradiskally, peridiskally, epidurally, perispinally, intraarticular or combinations thereof.

In various embodiments, because the combination of analgesic and/or anti-inflammatory agent is locally administered, therapeutically effective doses may be less than doses administered by other routes (oral, topical, etc.). In turn, systemic side effects, such as for example, liver transaminase elevations, hepatitis, liver failure, myopathy, constipation, etc. may be reduced or eliminated.

The drug depot can be delivered to any site beneath the skin, including, but not limited to, at least one muscle, ligament, tendon, cartilage, spinal disc, spinal foraminal space, near the spinal nerve root, or spinal canal.

In various embodiments, a method of treating or preventing postoperative pain or inflammation in a patient in need of such treatment is provided, the method comprising suturing one or more biodegradable drug depots comprising a therapeutically effective amount of an analgesic and/or anti-inflammatory agent or pharmaceutically acceptable salt thereof at or near a target tissue site beneath the skin, wherein the drug depot comprises at least one surface adapted to receive one or more sutures so as to limit movement of the drug depot at or near the target tissue site and the drug depot is capable of releasing the analgesic and/or anti-inflammatory agent or pharmaceutically acceptable salt thereof over a period of at least 3 days.

Another embodiment provides a method for treating a mammal suffering from inflammation and/or pain, said method comprising administering a therapeutically effective amount of at least one analgesic agent and at least one anti-inflammatory agent at a target site beneath the skin at or near the target site. The at least one analgesic agent and at least one anti-inflammatory agent may for example be administered locally to the target tissue site as a drug depot.

In some embodiments, the therapeutically effective dosage amount and the release rate profile are sufficient to reduce inflammation and/or pain for a period of at least one day, for example, 1-90 days, 1-10 days, 1-3 days, 3-7 days, 3-12 days; 3-14 days, 7-10 days, 7-14 days, 7-21 days, 7-30 days, 7-50 days, 7-90 days, 7-140 days, or 14-140 days.

In some embodiments the at least one analgesic agent and at least one anti-inflammatory agent or a portion of the at least one analgesic agent and at least one anti-inflammatory agent are administered as a bolus dose at the target tissue to provide an immediate release of the at least one analgesic agent and at least one anti-inflammatory agent.

In some embodiments there is a composition useful for the treatment of inflammation comprising an effective amount of at least one analgesic agent and at least one anti-inflammatory agent that is capable of being administered to e.g., a pain or inflammatory site. By way of example, they may be administered locally to the foraminal spine, paraspinal muscles or subcutaneous tissues.

In some embodiments, the at least one analgesic agent and/or at least one anti-inflammatory agent are administered by placement into an open patient cavity during surgery. In some embodiments, the drug depot can be placed at postions around the pain generator using a strategy of triangulation.

A strategy of triangulation may be effective when administering multiple depot pharmaceutical formulations. Thus, a plurality (at least two, at least three, at least four, at least five, at least six, at least seven, etc.) drug depots comprising the pharmaceutical formulations may be placed around the target tissue site (also known as the pain generator or pain generation site) such that the target tissue site falls within a region that is either between the formulations when there are two, or within an area whose perimeter is defined by a set of plurality of formulations.

In some embodiments, the formulation is implantable at or near a target tissue site at the time of surgery. The active ingredients may then be released from the depot via diffusion in a sustained fashion over a period of time, e.g., 1-3 days, 3-15 days, 5-10 days or 7-10 days post surgery in order to address pain and inflammation.

In some embodiments, a desired release profile is maintained for at least three days, at least ten days, at least twenty days, at least thirty days, at least forty days, at least fifty days, at least ninety days, at least one hundred days, at least one-hundred and thirty-five days, at least one-hundred and fifty days, or at least one hundred and eighty days.

In some embodiments, the drug depot may release 5%, 10%, 15%, 20%, 25%, 30%, 40%, 50%, 60%, 70%, 80%, 90%, 95%, or 99% of the at least one analgesic agent or pharmaceutically acceptable salt thereof and at least one anti-inflammatory agent or pharmaceutically acceptable salt thereof relative to a total amount of at least one analgesic agent or pharmaceutically acceptable salt thereof and at least one anti-inflammatory agent loaded in the drug depot over a period of at least three days, at least seven days, at least ten days, at least twenty days, at least thirty days, at least forty days, at least fifty days, at least ninety days, at least one hundred days, at least one-hundred and thirty-five days, at least one-hundred and fifty days, or at least one hundred and eighty days. In various embodiments, the analgesic will be released in an initial burst dose, then the analgesic will be released daily for 3 days and then stop (e.g., this will be suitable to reduce, prevent or treat, post-operative pain), while the anti-inflammatory agent will be released daily without a burst dose for 3 to 12 days, 5 to 10 days or 7 to 10 days after the drug depot is administered to the target tissue site.

In various embodiments, an implantable drug depot useful for reducing, preventing or treating pain and inflammation is provided in a patient in need of such treatment, the implantable drug depot comprising a therapeutically effective amount of an analgesic and/or an anti-inflammatory agent or pharmaceutically acceptable salts thereof, the depot being implantable at a site beneath the skin to reduce, prevent or treat pain and/or inflammation, wherein the drug depot (i) comprises one or more immediate release layer(s) that is capable of releasing about 5% to about 20% of the analgesic and the anti-inflammatory agent or pharmaceutically acceptable salts thereof relative to a total amount of the analgesic and the anti-inflammatory agent or pharmaceutically acceptable salts thereof loaded in the drug depot over a first period of up to 48 hours and (ii) one or more sustain release layer(s) that is capable of releasing about 21% to about 99% of the analgesic and the anti-inflammatory agent or pharmaceutically acceptable salts thereof relative to a total amount of the analgesic and/or the anti-inflammatory agent or pharmaceutically acceptable salts thereof loaded in the drug depot over a subsequent period of up to 3 days to 6 months or 3 days to 2 weeks.

By way of non-limiting example, the target tissue site may comprise at least one muscle, ligament, tendon, cartilage, spinal disc, spinal foraminal space near the spinal nerve root, facet or spinal canal. The target tissue may be associated with an acute disease or chronic disease or surgery.

In some embodiments, an implantable drug depot is provided, wherein the drug depot (i) comprises one or more immediate release layer(s) that releases a bolus dose of at least one analgesic agent or pharmaceutically acceptable salt thereof and at least one anti-inflammatory agent or pharmaceutically acceptable salt thereof at a site beneath the skin and (ii) one or more sustain release layer(s) that releases an effective amount of at least one analgesic agent or pharmaceutically acceptable salt thereof and at least one anti-inflammatory agent or pharmaceutically acceptable salt thereof over a period of 3 days to 6 months. By way of example, in the drug depot, the one or more immediate release layer(s) may comprise poly (lactide-co-glycolide) (PLGA) and the one or more sustain release layer(s) may comprise polylactide (PLA).

Method of Making

In various embodiments, the drug depot comprising the active ingredients can be made by combining a biocompatible polymer and a therapeutically effective amount of the active ingredients or pharmaceutically acceptable salts thereof and forming the implantable drug depot from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: the active ingredients, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, certain therapeutic agents may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the active ingredient containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., clonidine), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of certain active ingredients, such as an anti-inflammatory and analgesic because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion processes may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., pellet, strip, etc.) is cooled. Examples of cooling processes include air cooling and/or immersion in a cooling bath. In some embodiments, a water bath is used to cool the extruded depot. However, where a water-soluble therapeutic agent such as active ingredients are used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired. Thus, a sustained release region of the drug depot may, in various embodiments, be made by immediately removal of water or moisture.

In various embodiments, the drug depot can be prepared by mixing or spraying the drug with the polymer and then molding the depot to the desired shape. In various embodiments, active ingredients are used and mixed or sprayed with the PLGA or PEG550 polymer, and the resulting depot may be formed by extrusion and dried.

The drug depot may also comprise combining a biocompatible polymer and a therapeutically effective amount of at least one analgesic agent or pharmaceutically acceptable salt thereof and at least one anti-inflammatory agent or pharmaceutically acceptable salt thereof and forming the implantable drug depot from the combination.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A drug depot implantable at or near a target tissue site beneath the skin of a patient, the drug depot being biodegradable and comprising a therapeutically effective amount of a drug and one or more channels adapted to receive one or more sutures so as to limit movement of the drug depot at or near the target tissue site, the drug being distributed homogenously throughout the drug depot and having a particle size of about 1 micrometer to about 250 micrometers, wherein (i) the drug depot is capable of releasing the therapeutically effective amount of the drug over a period of at least one day, and (ii) the suture is biodegradable and further comprises a first region comprising a knot, bead, tab or clip having a larger diameter than the one or more channels that prevents the first region of the suture from passing through the one or more channels and a second region comprising a knot, bead, tab or clip having a larger diameter than the one or more channels that upon application of a pulling force, the second region of the suture pulls through the one or more channels to limit movement of the drug depot.

2. A drug depot according to claim 1, wherein the first region of the suture comprises a knot that prevents the suture from passing through the channel, and the second region of the suture also comprises a knot.

3. A drug depot according to claim 1, wherein the drug depot comprises a first channel disposed at a first end of the drug depot adapted to receive the biodegradable suture and a second channel disposed at a second end of the drug depot adapted to receive the same biodegradable suture after the suture contacts the target tissue site so as to anchor the depot at or near a target tissue site.

4. A drug depot according to claim 1, wherein the suture degrades faster than the drug depot.

5. A drug depot according to claim 1, wherein the one or more channels comprise a portion of biodegradable suture disposed within the one or more channels so that the biodegradable suture is pre-threaded in the one or more channels.

6. A drug depot according to claim 1, wherein the drug comprises an analgesic and/or anti-inflammatory agent or pharmaceutically acceptable salts thereof and the drug depot is adapted to release the drug over a period of at least 1 day to treat post-operative pain.

* * * * *

UNITED STATES PATENT AND TRADEMARK OFFICE
CERTIFICATE OF CORRECTION

PATENT NO.         : 8,202,531 B2
APPLICATION NO.    : 12/178106
DATED              : June 19, 2012
INVENTOR(S)        : McKay Page 1 of 1

It is certified that error appears in the above-identified patent and that said Letters Patent is hereby corrected as shown below:

In Column 5, Line 51, delete "mepiridine," and insert -- meperidine, --, therefor.

In Column 22, Line 51, delete "LIG" and insert -- L/G --, therefor.

In Column 22, Line 56, delete "LUG" and insert -- L/G --, therefor.

In Column 22, Line 58, delete "LIG" and insert -- L/G --, therefor.

In Column 22, Line 63, delete "LIG" and insert -- L/G --, therefor.

In Column 25, Line 25, delete "steal," and insert -- steel, --, therefor.

In Column 27, Line 26, delete "postions" and insert -- positions --, therefor.

Signed and Sealed this
Seventh Day of August, 2012

David J. Kappos
*Director of the United States Patent and Trademark Office*